(12) United States Patent
Best et al.

(10) Patent No.: US 9,874,737 B2
(45) Date of Patent: Jan. 23, 2018

(54) METHOD AND APPARATUS FOR COMBINATION OF LOCALIZATION MICROSCOPY AND STRUCTURED ILLUMINATION MICROSCOPY

(71) Applicant: Forschungszentrum Mikroskopie (FZM), LuciaOptics gemeinnützige UG, Karlsruhe (DE)

(72) Inventors: Gerrit Best, Koblenz (DE); Christoph Cremer, Heidelberg (DE); Sabrina Rossberger, Heidelberg (DE); Stefan Dithmar, Dossenheim (DE)

(73) Assignee: FORSCHUNGSZENTRUM MIKROSKOPIE (FZM), LUCIAOPTICS GEMEINNÜTZIGE UG, Karlsruhe (DE)

( * ) Notice: Subject to any disclaimer, the term of this patent is extended or adjusted under 35 U.S.C. 154(b) by 66 days.

(21) Appl. No.: 14/890,243

(22) PCT Filed: May 7, 2014

(86) PCT No.: PCT/EP2014/001228
§ 371 (c)(1),
(2) Date: Nov. 10, 2015

(87) PCT Pub. No.: WO2014/180566
PCT Pub. Date: Nov. 13, 2014

(65) Prior Publication Data
US 2016/0124208 A1    May 5, 2016

(30) Foreign Application Priority Data
May 10, 2013 (EP) .................................. 13002490

(51) Int. Cl.
*G02B 21/36* (2006.01)
*G01N 21/64* (2006.01)
(Continued)

(52) U.S. Cl.
CPC ....... *G02B 21/367* (2013.01); *G01N 21/6458* (2013.01); *G02B 21/0076* (2013.01);
(Continued)

(58) Field of Classification Search
CPC  G02B 21/00; G02B 21/0004; G02B 21/0032; G02B 21/0076; G02B 21/06;
(Continued)

(56) References Cited

U.S. PATENT DOCUMENTS

2009/0115244 A1  5/2009  Schluter
2010/0315708 A1* 12/2010  Amberger .............. G02B 21/06
                                                             359/389

(Continued)

FOREIGN PATENT DOCUMENTS

DE    102006047912 A1    4/2008
DE    102008009216 A1    8/2009
(Continued)

OTHER PUBLICATIONS

Folling et al., "Fluorescence nanoscopy by ground-state depletion and single-molecule return", Nature Methods, vol. 5, No. 11, Nov. 2008, pp. 943-945.*

(Continued)

*Primary Examiner* — Stephone B Allen
*Assistant Examiner* — Adam W Booher
(74) *Attorney, Agent, or Firm* — Armstrong Teasdale LLP

(57) ABSTRACT

A fluorescence microscope for obtaining super-resolution images of a sample labeled with at least one fluorescent label by combining localization microscopy and structured illumination microscopy is provided. The fluorescence microscope includes one or more light sources, an illumination system having a structured illumination path for illuminating the sample with structured illumination light and a localiza-
(Continued)

tion illumination path for illuminating the sample with localization illumination light.

7 Claims, 5 Drawing Sheets

(51) Int. Cl.
*G02B 21/00* (2006.01)
*G02B 21/16* (2006.01)
*G02B 27/58* (2006.01)

(52) U.S. Cl.
CPC .......... *G02B 21/16* (2013.01); *G02B 21/361* (2013.01); *G02B 27/58* (2013.01); *G01N 21/6445* (2013.01); *G01N 2201/0675* (2013.01)

(58) Field of Classification Search
CPC ........ G02B 21/16; G02B 21/18; G02B 21/36; G02B 21/361; G02B 21/365; G02B 21/367; G02B 27/58; G01N 21/62; G01N 21/63; G01N 21/64; G01N 21/6428; G01N 21/6445; G01N 21/6447; G01N 21/6456; G01N 21/6458; G01N 2201/063; G01N 2201/0635; G01N 2201/067; G01N 2201/0675
See application file for complete search history.

(56) References Cited

U.S. PATENT DOCUMENTS

| 2011/0109736 A1* | 5/2011 | Mertz | G06T 5/20 348/79 |
| 2012/0046203 A1* | 2/2012 | Walsh | A61B 5/157 506/39 |
| 2013/0068967 A1* | 3/2013 | Kleppe | G01N 21/6458 250/459.1 |

FOREIGN PATENT DOCUMENTS

| DE | 102008054317 A1 | 5/2010 |
| DE | 102011177269 A1 | 12/2012 |
| WO | 2009115244 A1 | 9/2009 |
| WO | 2013053859 A1 | 4/2013 |

OTHER PUBLICATIONS

Grotjohann et al., "Diffraction-unlimited all-optical imaging and writing with a photochromic GFP", Nature, vol. 478, Oct. 2011, pp. 204-208.*
Klar et al., "Subdiffraction resolution in far-field fluorescence microscopy", Optics Letters, vol. 24, No. 14, Jul. 1999, pp. 954-956.*
ISR/WO, PCT/EP2014/001228 filed May 7, 2014, 4 pages.

* cited by examiner

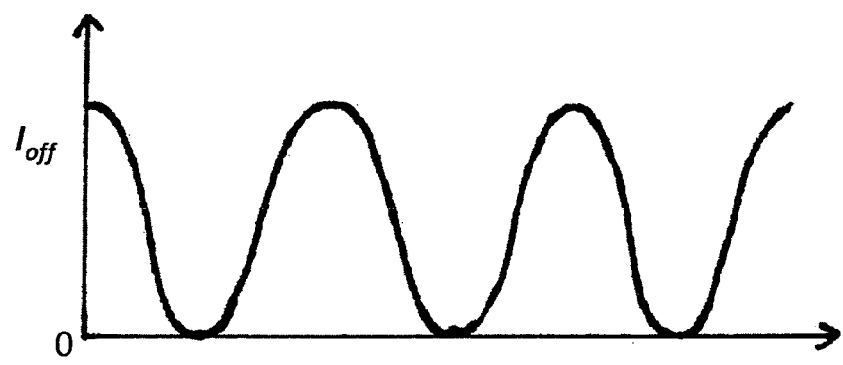
Fig. 2a
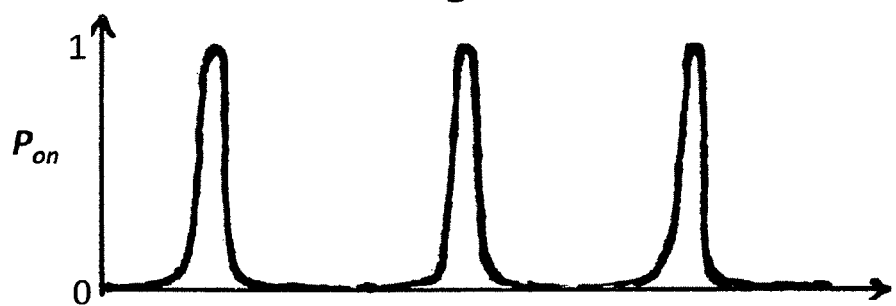
Fig. 2b
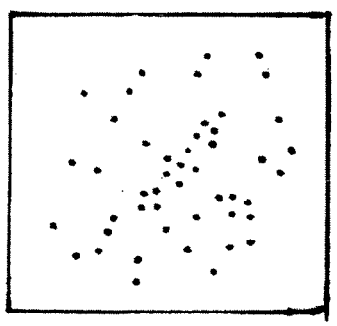 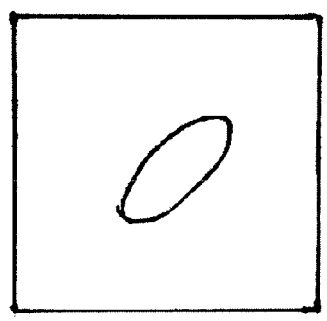 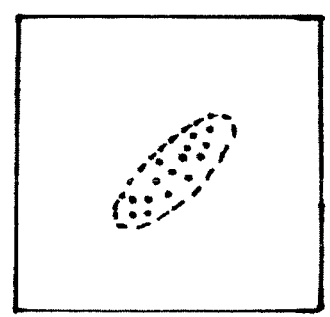
Fig. 3a  Fig. 3b  Fig. 3c

METHOD AND APPARATUS FOR COMBINATION OF LOCALIZATION MICROSCOPY AND STRUCTURED ILLUMINATION MICROSCOPY

CROSS REFERENCE TO RELATED APPLICATIONS

This application is a National Stage Entry of PCT/EP2014/001228 filed May 7, 2014, which claims priority from European Patent Application No. EP 13002490.4 filed May 10, 2013, both of which are incorporated herein in their entirety.

BACKGROUND

The present invention relates to a fluorescent microscope and a respective method for obtaining super-resolution images of a sample labelled with at least one type fluorescent label by combining localization microscopy and structured illumination microscopy.

The ability of a microscope to distinguishably image small, "point-like" objects is characterized, besides by the contrast, by the resolving power or resolution of the microscope. Due to the diffraction, point objects are seen as blurred disks (called Airy disks) surrounded by diffraction rings. The resolution of a microscope can be defined as the ability to distinguish between two closely spaced Airy disks. In other words, the resolution of a microscope can be defined as the ability to reveal adjacent structural details as distinct and separate. The diffraction limits this ability and thus the resolution. The extent and magnitude of the diffraction patterns are affected by both the wavelength of light $\lambda$ and the numerical aperture (NA) of the objective lens. Thus, there is a finite limit beyond which it is impossible to resolve separate points in the object field, known as the diffraction limit or "Abbe/Rayleigh limit".

Although the Abbe/Rayleigh limit is a universal principle that cannot be broken directly, multiple techniques, including fluorescence microscopy techniques, for surpassing it have been proposed. Contrary to normal transilluminated light microscopy, in fluorescence microscopy the observed sample (specimen or object) is illuminated through an objective lens with a narrow set of wavelengths of light. This light interacts with fluorophores in the sample which then emit light of a different wavelength, thereby forming an image of the observed specimen.

One technique to improve the resolution beyond the Abbe/Rayleigh limit is based on illumination of the sample with structured illumination light. Structured illumination microscopy (SIM or SMI) methods rely on coding high resolution information into the low resolution supported region of the microscope to circumvent the Abbe/Rayleigh limit. The required conditions are generated in structured illumination microscopy by illuminating the object with a periodic pattern and observing fluorescent light emitted by the illuminated sample. An example of a super-resolution fluorescent microscope using structured illumination light is disclosed in US 2010/0315708.

Another conceptually different technique to surpass the Abbe-Rayleigh limit based on Spectral Precision distance Microscopy (SPDM) or Localization microscopy (LM) is disclosed US 2009/115244 A1. The underlying principle of the SPDM/LM approach is the "optical isolation" in space and/or time domain and hence the independent localization of individual, "point-like" objects due to any photon-based characteristics of the emitted light. This means that in a given diffraction limited observation volume defined for example by the Full-Width-at-Half-Maxima (FWHM) of the Point Spread Function (PSF) of the microscope system used, at a given time interval and for a given spectral registration mode, only one point-like object (for example a single fluorescent or autofluorescent molecule) or (under certain conditions) only few objects are registered. By imaging fluorescent bursts of individual point-like objects (e.g. molecules) after excitation, the position of the point-like objects may be determined with a precision much higher than the FWHM of the PSF. The final super-resolution image is obtained by registration of multiple (up to thousands) of images of the same sample (or region of interest of a sample), so that the optical resolution is improved by "scanning" the fourth coordinate of the space-time continuum.

In fluorescent microscopes using structured illumination through an objective there is usually a substantial reduction of the intensity of the illumination light due to the employment of a system for generating structured illumination light. If the system for generating structured illumination light is an interferometric system (such as for example described in US 2010/0315708), there is a reduction of the initial light intensity of at least 50%. If diffraction gratings or spatial light modulators (SLM) are used to generate structured illumination light, the reduction in light intensity can be even higher.

For carrying out localization microscopic measurements, on the other hand, usually illumination light having high intensity is required, in order to assure sufficiently high photon yield. Thus for example, if the sample is labelled with "conventional" fluorophores, illumination light having high intensity in the range of about 10 kW/cm$^2$ to about 1 MW/cm$^2$ is needed in order to transfer the fluorescent molecules in a metastable dark state. If special photo-switchable fluorophores are used to label the sample, this initial illumination with high intensity light is not necessary. However, even in this case a read-out light with high intensity is needed, in order to sufficiently fast bleach out the individual activated fluorophores before new fluorophores are brought into the fluorescent state. An illumination light with low intensity results in a very long acquisition time. This problem is typical for many imaging fluorescent techniques.

In order to realise illumination of the sample with high intensity illumination light a high power laser is usually required. In addition, the size of illuminated region of the sample is usually very small. A reduction of the size of the illuminated region of the sample may be realized for example by an additional converging lens in the illumination path. Alternatively it is possible to use an optical set-up in which the laser light is not expanded, but is directly directed to the microscope objective instead. Still another option is to use a very low beam expansion, which is untypical for the fluorescent microscopy. In all cases the size of illuminated region of the sample in the localization microscopy is at best about 100 µm$^2$. However, this reduces the amount of information acquired at each measurement. Thus, it is desirable to provide methods and apparatuses enabling the analysis of as large illuminated region as possible.

For the above reasons a combination of structured illumination microscopy and localization microscopy was considered very difficult, since either the intensity of the illumination light is too low for localization microscopy measurements or the size of the illuminated region of the sample is too small for structured illumination measurements.

BRIEF DESCRIPTION

The systems and methods described herein alleviate the above problems and provide an improved fluorescence microscope and a method for obtaining super-resolution images of a fluorescently labelled sample.

According to one aspect, a fluorescence microscope for obtaining super-resolution images of a sample labeled with at least one fluorescent label by combining localization microscopy and structured illumination microscopy is provided. The microscope includes one or more light sources, an illumination system having a structured illumination path for illuminating the sample with structured illumination light and a localization illumination path for illuminating the sample with localization illumination light.

The illumination system includes a switching mechanism configured between at least a first, a second and/or a third mode, wherein in the first mode at least a portion of the light emitted from the one or more light sources propagates through one of the illumination paths, in the second mode at least a portion of the light emitted from the one or more light sources propagates through the other one of the illumination paths, and in the third mode at least a portion of the light emitted from one or more of the light sources propagates through one illumination path while simultaneously at least another portion of the light emitted from one or more of the light sources propagates through the other illumination path, a pattern generation system positioned in the structured illumination path configured to spatially modulate the intensity of the light in at least one, for example in two- or three orthogonal spatial directions, which entered the structured illumination path, thereby generating the structured illumination light, and at least one image detector positioned in an optical detection path, configured to detect at least a portion of fluorescent light emitted from activated fluorescent molecules of the illuminated sample, thereby obtaining an image of the sample.

According to another aspect there is provided a method for obtaining super-resolution image data of a sample labeled with at least one type of fluorescent label by using a combination of localization microscopy and structured illumination microscopy.

The method for obtaining super-resolution image data of a sample labeled with at least one type of fluorescent label may be carried out by using a fluorescent microscope. The method includes illuminating the sample, thereby exciting at least a portion of the fluorescent molecules of the at least one fluorescent label to emit fluorescent light, the illuminating including illuminating the sample with localization illumination light (for example through the localization illumination path of the fluorescent microscope), and/or illuminating the sample with structured illumination light (for example through the structured illumination path of the fluorescent microscope), detecting at least a portion of the fluorescent light emitted from the excited fluorescent molecules of the at least one fluorescent label, thereby obtaining at least one image of the illuminated sample, processing the obtained at least one image of the sample image to obtain a super-resolution image of the sample or a super-resolution image data.

The structured illumination light may be light, the intensity of which is spatially modulated in at least one spatial direction, for example in two- or three orthogonal spatial directions.

The fluorescence microscope and the method for obtaining super-resolution images of a sample according to the disclosure may advantageously provide a solution to the two basic problems of the fluorescent microscopy mentioned above: either too low intensity of the illumination light or too small size of the illuminated region of the sample.

Advantageously, it is possible to carry out individual structural illumination microscopy (SIM/SMI) and localization microscopy (LM) measurements as well as modified localization microscopy measurements, which utilize structured illumination light with the same optical set-up. Accordingly, a fluorescence microscope with a less costly, less critical and more stable optical setup as compared to prior art solutions may be realized.

Further, the combination of the two different microscopic techniques, localization microscopy and structured illumination microscopy, in a single optical set-up allows to easily obtain images of the same region of interest in the object (sample) plane (x,y) and in the same (coinciding) z-planes by both methods. This is very difficult if not impossible to realize with two different optical set-ups: one for localization microscopy and one for structured illumination microscopy. The possibility to obtain images of the same region of the sample in the same coinciding z-plane may considerably improve the precision of the measurements and the ability to visualize and/or obtain structural information of complex, three-dimensional samples. Accordingly, high resolution three-dimensional images of the sample or respectively high resolution three-dimensional structural data with improved accuracy may be obtained.

According to an aspect, it is possible to obtain improved super-resolution images and super-resolution image data showing both structural data and exact localization data by correlating an image obtained by structured illumination microscopy with an image obtained by localization microscopy.

In addition, the proposed modified localization microscopy technique using structured illumination light during the process of obtaining/collecting localization illumination data (for example as structured read-out (excitation light) or structured deactivation light) surprisingly allows further increase of the resolution and localization precision in comparison with conventional localization methods using non-structured illumination light. In an example the resolution may be improved by a factor of about 3 to 4 in comparison with conventional localization methods.

In view of the above advantages, the fluorescent microscope and a method for obtaining a super-resolution image of a sample may be useful for many applications, for example in the field of contactless diagnostics, particularly in cellular biology, medicine (for example tissue diagnostics, dermatology, dentistry, endoscopy, embryology, ophthalmology, etc.), the investigation of model organisms and various other in-vivo observations.

Some possible applications may be the visualization of single gene domains; the replication factories responsible for the doubling of the cellular DNA; the repair complexes responsible for the repair of environmentally induced genome alterations; the chromatin remodelling/silencing complexes responsible for the expression related modification of genome nanostructure; the transcription factories allowing the "reading" of the genetic code; the splicing factories processing the transcribed RNA; the nuclear pore complexes controlling the traffic between cell nucleus and the rest of the cell; the ribosomes translating RNA into proteins; the proteasomes controlling the decomposition of proteins; the ion channel complexes controlling the transport of ions across the cell membrane; or the cell junction complexes responsible for formation of tissues.

The combination of the two methods (localization microscopy and structured illumination microscopy) is particularly suitable for obtaining images of autofluorescent structures in a sample in combination with conventional labelling methods. In particular, the structured illumination microscopy may be utilized for visualizing structures in a sample by detecting the (often broad band) autofluorescent light emitted by autofluoresent fluorophores within different structures of the sample, such as for example retina proteins, lipofuszin-granula, etc. Generally, such images cannot be obtained by means of localization microscopy due to the lacking switching capabilities of the autofluorescent fluorophores. In addition, by carrying out localization microscopy measurements, it is possible to visualize additional, previously labelled structures or compartments. To this extent the illumination may be switched to localization illumination mode, in which the light propagates through the localization illumination light. Since the autofluorescent fluorophores generally exhibit little bleaching even at high illumination intensities and cannot be switched between a bright and a dark state, it is possible to separate the image data obtained by structured illumination microscopy from the image data obtained by localization microscopy. A subsequent overlay of the structured illumination microscopy data enables simultaneous visualization of both autofluorescent structures and fluorescently labelled structures within the observed sample. If by means of suitable mathematical methods the localisation image data are converted into corresponding structural data, it is possible to combine in one image both autofluorescent structure data/information and structure data/information obtained from the localization image data.

The above and other features and advantages of the present disclosure will become more apparent upon reading of the following detailed description of example embodiments and accompanying drawings. It should be understood that even though embodiments are separately described, single features and functionalities thereof may be combined without prejudice to additional embodiments.

BRIEF DESCRIPTION OF THE DRAWINGS

Example embodiments of are exemplarily described regarding the following figures.

FIG. 1b: phase $\Phi_2$; FIG. 1c: phase $\Phi_3$) for excitation of the individual fluorescent molecule;

FIGS. 2a and 2b show an example of the application of deactivating structured illumination light, wherein FIG. 2a shows the intensity of the deactivating structured illumination light as a function of the x spatial direction; and FIG. 2b shows the probability $P_{on}$ that a given fluorescent molecule remains in an activated state (on-state) upon illumination with the structured illumination pattern shown in FIG. 2a.

FIGS. 3a-3c show an example of correlating structured illumination microscopy images and localization microscopy images, wherein FIG. 3a shows an exemplary localization microscopy image composed of the detected individual fluorescent signals;

FIG. 3b shows an exemplary mask of one relevant region of interest obtained on the basis of the structured illumination microscopy image;

FIG. 3c shows the localization microscopy image to which the mask shown in FIG. 3b is applied.

FIGS. 5a-6c show exemplary optical layouts of different structured illumination paths of a fluorescent microscope, wherein FIG. 5a shows a structured illumination path including an interferometer;

FIG. 6 shows an exemplary localization illumination path.

Throughout the figures, same reference signs are used for the same or similar elements.

DETAILED DESCRIPTION

Figure 1A:
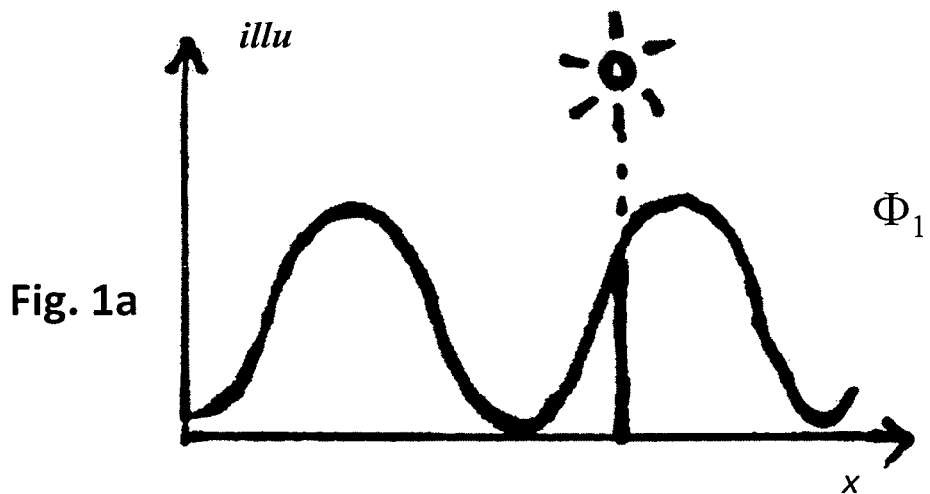
FIGS. 1a-1c show an example of using spatially modulated read-out light with different phases $\Phi_1$, $\Phi_2$ and $\Phi_3$ (FIG. 1a: phase $\Phi_1$.

The term "fluorescence" within the scope of the present application, is to be understood as any photon-interaction wherein there are differences between the illumination, respectively excitation spectrum, and the emission spectrum of the same object which cannot be explained based on the monochromatic absorption only. That includes for example in particular multiphoton interactions, by which the excitation wavelengths can be greater than the emission wavelengths. Thus the term fluorescence will be also used in the sense of this application for the closely related phenomena as "luminescence" and "photophosphorescence" or short "phosphorescence". This includes in particular the cases of longer fluorescence duration, for example in the millisecond range. The use of phosphorescent optical labels, respectively the use of phosphorescent molecules for optical labeling instead of fluorescent molecules may be for example advantageous in view of improving the in vivo applicability of the proposed methods, since these molecules allow for localization over a longer period of time.

Under the term "fluorescence molecule" within the scope of the present application, it is to be understood any "point-like" fluorescent element, that is to say any fluorescent element having size considerably smaller than the wavelength of the employed illumination, respectively excitation light), which is suitable for labeling of the measured sample.

The term "fluorescent label" encompasses any type of fluorescent labels, including autofluorescent labels and/or naturally occurring autofluorescent substances. The expression "different types of fluorescent labels" refers to fluorescent labels having different spectral signatures. In this context, "spectral signature" means any photophysical property, such as for example fluorescent spectrum, absorption, lifetime, etc., which can be used for optically discriminated registration.

The term "super-resolution" means spatial resolution in at least one spatial direction, which is higher than the "Abbe/Rayleigh" limit, i.e. higher than the diffraction limit for the specific optical system and illumination wavelength(s).

According to an example, a fluorescence microscope for obtaining super-resolution images of a sample labeled with at least one fluorescent label by combining localization microscopy and structured illumination microscopy includes: one or more light sources, an illumination system having a structured illumination path for illuminating the sample with structured illumination light and a localization illumination path for illuminating the sample with localization illumination light, wherein the illumination system includes: a switching mechanism configured to switch between a first, a second and/or a third mode, wherein in the first mode at least a portion of the light emitted from the one or more light sources propagates through one of the illumination paths, in the second mode at least a portion of the light emitted from the one or more light sources propagates through the other one of the illumination paths, and in the third mode at least a portion of the light emitted from one or more of the light sources propagates through one illumination path while simultaneously at least another portion of the light emitted from one or more of the light sources propagates through the other illumination path, a pattern generation system positioned in the structured illumination path configured to spatially modulate the intensity of the light which entered the structured illumination path in at least one spatial direction, for example in two- or three orthogonal spatial directions, thereby generating the structured illumination light, at least one image detector positioned in an optical detection path, configured to detect at least a portion of fluorescent light emitted from fluorescent molecules of the illuminated sample, thereby obtaining an image of the sample.

The microscope may include at least one light source, for example a laser emitting a predetermined wavelength, a light emitting diode (LED), a gas discharge lamp, etc. In an example, the microscope may include a plurality of light sources, each emitting light with different wavelengths. The light emitted from the light sources is directed towards the sample to illuminate it by means of an illumination system including optical elements defining localization illumination path and a structured illumination path. The illumination of the sample may be carried out either continually or discontinually.

The wavelength and/or intensity of the localization illumination light and structured illumination light and/or the duration of illumination of the sample with localization illumination light and structured illumination light may be suitably selected and optionally adjusted depending for example on the type of fluorescent label used, the sample itself, the characteristics of the image detector, and other factors.

The switching mechanism may be configured to switch between at least two of the first, the second and the third mode, for example upon receiving a signal from a control mechanism or based on a predetermined switching pattern. In an embodiment, the switching mechanism may be configured to switch among all three modes.

The switching mechanism may be realized by or may include one or more optical elements such as movable (translatable and/or rotatable and/or foldable) mirrors, beam splitters, chromatic beam splitters, polarising beam splitters, electro-optical modulators (EOM), accousto-optical modulators (AOM), etc. The switching mechanism may further include additional optical elements such as aperture stops, filters, mirrors, spatial light modulators (SLM), etc.

In an example the switching mechanism may be realized by a movable (e.g. rotatable and/or translatable) beam splitter and/or a mirror. In another example polarizing beam splitters and/or mirrors may be used. Polarising beam splitters, in particular in combination with other polarization controlling optical elements (such as electro-optical modulators), allow switching between the different modes of operation (i.e. between the different illumination paths) based on the light polarization. In particular, by controlling the light polarization, the portion of the light propagating through the respective illumination path may be controlled. The use of electro-optical modulators (EOM) allows for a very fast switching between the different modes of operation (i.e. between the different illumination paths), generally in µs to ns range. This may be particularly advantageous in a fluorescent microscope configured to carry out the modified localization microscopy methods using structured illumination light during the acquisition of a localization microscopy image of the sample (i.e. during the localization microscopy measurement) described in detail further on. If chromatic-beams splitters or mirrors are used and the light source emits at least two wavelengths, it is possible to direct one of the wavelengths to the structured illumination path and the other to the localization illumination path.

In an example the switching mechanism may be configured to switch at least between the first mode and the second mode.

For example in the first mode at least a portion of the light emitted from the one or more light sources may propagate through the localization illumination path, thereby illuminating the sample with localisation illumination light. In the second mode the at least a portion of the light emitted from the one or more light sources may be diverted to enter in and propagate through the structured illumination path, thereby illuminating the sample with structured illumination light. The switching mechanism may, however, be configured such that in the first mode, at least a portion of the light emitted from the one or more light sources enters in and propagates through the structured illumination path, whereas in the second mode it propagates the localization illumination path. The switch between the illumination paths may be realized for example by movable mirrors, beam-splitters, polarizing beam splitters, etc.

In another example, the switching mechanism may configured to switch at least between the first mode (wherein at least a portion of the light emitted from one or more of the light sources propagates either through the structured illumination path or thought the localization illumination path) and the third mode (wherein at least a portion of the light emitted from one or more of the light sources propagates through both the structured and the illumination path, thereby simultaneously illuminating the sample with both structured illumination light and localization illumination light). This may be realized for example by using a chromatic and/or polarizing beam splitter or by other suitable means.

The structured illumination path (i.e. the optical elements constituting or defining the structured illumination path) is configured and arranged to produce structured illumination light for illuminating the sample, the intensity of said structured illumination light being spatially modulated in at least one, for example in two- or three orthogonal spatial directions. This may be achieved by a pattern generation system arranged in the structured illumination path. In an example, structured illumination path (in particular the pattern generation system) may be configured to produce structured illumination light which is spatially modulated in a plane, for example in a plane which is orthogonal to the direction of propagation of the structured illumination light beam. In addition or as an alternative, the pattern generation system may be configured to produce structured illumination light which is spatially modulated in a third direction, for example in the direction of propagation of the structured illumination light beam. It is also possible to configure the structured illumination path (in particular the pattern generation system) to switch between the two modes of producing structured illumination light.

The pattern generation system may consist of or include one or more spatial light modulators (SLM), one or more diffraction gratings, etc. In an example the spatial light modulator or the diffraction grating may be arranged in a conjugated object plane, i.e. in a plane, which is imaged (respectively focused or projected) in the object plane (i.e. on the plane in which the sample (object) is arranged). An advantage of using spatial light modulator(s) is the ability to project arbitrary patterns in the object plane. The pattern generation system may also be realized by means of an interferometer, such as Michelson interferometer, Twyman-Green interferometer, etc. The interferometer may be configured as Total Internal Reflection interferometer (TIRF/LSI-TIRF).

The pattern generation system may be configured to control or shift the phase of the structured illumination pattern and/or to move (for example translate and/or rotate) the structured illumination pattern. This may be realized for example by using translatable and/or rotatable mirrors, beam splitters or other mechanically translatable and/or rotatable elements such as translational and/or rotational tables or optical element holders. Spatial light modulators have the advantage that the pattern may be phase shifted or moved without mechanically moving parts. If diffraction gratings are used, it is possible to phase-shift (i.e. to move) the structured illumination pattern by translating the diffraction grating. A rotation of the pattern can be realised by a mechanical rotation of the grating or by a (fast) switching between two or more gratings whose structures are rotated in respect to each other.

The localization illumination path (i.e. the optical elements constituting or defining the localization illumination path) is configured and arranged to produce localization illumination light with suitable wavelength and/or intensity for illuminating the sample. The localization illumination light may be homogeneous, i.e. non-structured or non-patterned. The localization illumination path (i.e. the optical elements constituting or defining the localization illumination path) may be configured such that the intensity of the localization illumination light is higher than the average or maximum intensity of the structured illumination light.

There are various ways to realize the localization illumination path, such that the localization illumination light has intensity, which is suitable to carry out localization microscopy measurements. Thus, according to an example, it is possible to direct a collimated, but not expanded light beam from the light source to the localization illumination path. The non-expanded light beam from the light source propagates through the localization illumination path, may optionally propagate through a focusing lens and is directed onto the sample by means of a microscope objective. In this case, the collimated, non-expanded light beam may propagate through the localization illumination path without having to pass through additional refractive elements (such as lenses) arranged in the localization illumination path, which reduce the beam's diameter, thereby increasing its intensity. It is, however, also possible to use an additional focusing lens arranged in the localization illumination path to focus the localization illumination light beam to set the beam diameter in the object plane to arbitrary values. This has the advantage that the light intensity in the object plane can be adjusted to the specific specimen over a wide range. It is also possible to use a telescope or a telescopic system arranged in the localization illumination path, in order to reduce the diameter of the light beam in the localization illumination path. In such cases the light beam emitted from the one or more light sources may be expanded (for example by a collimator, a telescope or by other means) prior to entering the localization illumination path and the structured illumination path.

The illumination system may include an illumination adjustment unit configured to adjust or control the intensity of the localization illumination light and/or structured illumination light. Alternatively or in addition the illumination adjustment unit may be configured to adjust the angle of illumination of the sample with localization illumination light and/or structured illumination light. Still further alternatively or in addition, the illumination adjustment unit may be configured to adjust the duration of illumination of the sample with the localization illumination light and/or structured illumination light.

The illumination adjustment unit may include one or more optical elements, such as lenses or lens systems, telescopes, collimators, filters, modulators (e.g. electro-optical modulators, accousto-optical modulators), rotatable mirrors, etc.

In particular, the illumination adjustment unit may include a localization illumination adjustment unit configured to adjust or control the intensity of the localization illumination light, and/or the angle of illumination of the sample with localization illumination light and/or the duration of illumination of the sample with localization illumination light. In an example, the localization illumination control unit may include at least one optical element configured to reduce or to expand the diameter of the light beam in the localization illumination path, such as for example collecting/converging lens, a telescope/a telescopic system, a diverging lens, positioned in the localization illumination path. For example, by reducing the diameter of the light beam in the localization illumination path the light intensity of the localization illumination light may be increased to a level suitable to carry out localization microscopy image acquisition.

The localization illumination adjustment unit may be configured to adjust the angle of illumination of the sample with localization illumination light. Accordingly, the localization illumination path may comprise one or more movable (e.g. rotatable and/or translatable) mirrors, beam splitters or other optical elements. In an example, the localization illumination path may be "reflected" at a rotatable mirror surface, which is positioned in a conjugated image plane. The mirror surface may be rotatable around at least one axis. It is thus possible to obliquely illuminate the sample with localization illumination light and/or adjust the angle of illumination of the sample. If the angle of illumination is appropriately selected, it is possible to achieve a total internal reflection at the interface between the glass coverslip and the sample or respectively the medium in which the sample is embedded. Thus, only fluorophores in a thin layer of the sample at the interface to the coverslip are excited by the evanescent electromagnetic field of the localization illumination light. It is thus possible to realize optical sectioning.

The localization illumination adjustment unit may also be configured to adjust the duration of illumination of the sample with localization illumination light. To this extent the localization illumination unit may comprise a suitable optical switch, which may be integrated within the switching mechanism.

The illumination adjustment unit may include a structured illumination adjustment unit configured to adjust or control the intensity of the structured illumination light, and/or the angle of illumination of the sample with structured illumination light, and/or the duration of illumination of the sample with structured illumination light. In an example, the structured illumination control unit may include at least one optical element configured to reduce or expand the diameter of the light beam in the structured illumination path, such as for example collecting/converging lens, a telescope/a telescopic system positioned in the structured illumination path.

The structured illumination adjustment unit may be configured to adjust the angle of illumination of the sample with structured illumination light. To adjust the angle or illumination of the sample with structured illumination light, the structured illumination adjustment unit may include one or more movable (e.g. rotatable and/or translatable) mirrors, beam splitters, lenses or other optical elements. In an example, the structured illumination adjustment unit may be a part of the pattern generation system. For example, if the pattern generation system is constituted by a Michelson-Moore or Twyman-Green type interferometer, the adjustment of the angle at which the sample is illuminated with structured illumination light may be realized by a rotatable beam splitter and/or at least one movable (e.g. rotatable and/or translatable) mirror.

The structured illumination adjustment unit may also be configured to adjust the duration of illumination of the sample with structured illumination light. Accordingly, the structured illumination unit may include a suitable optical switch, which may be integrated within the switching mechanism.

The fluorescent microscope may further include an objective through which the sample is illuminated by localization illumination light and/or structured illumination light. The objective may include at least one lens. Typically the objective comprises a plurality of lenses configured and arranged such as to reduce refractive and/or chromatic aberrations. The objective may be an achromat. The objective may be also a part of the detection path, i.e. the fluorescent light emitted from the fluorescent molecules of the sample may pass through the objective and be subsequently detected by the image detector.

The fluorescent microscope may include a dichroic filter and/or beam splitter and/or other optical elements configured to separate the illumination light from the fluorescent light emitted from the fluorescently labelled sample.

The image detector may be any two-dimensional detector, for example a CCD camera. The image detector may obtain a plurality of images of the illumination sample, on the basis of which a final super-resolution image or super-resolution image data may be obtained, in the manner described below in more detail. The super-resolution image data obtained by processing the at least one detected image may include structural information (i.e. information about the size, form and/or spatial location of one or more structures or objects in the observed sample) and/or positional information of the individual fluorescent molecules of the at least one fluorescent label, wherein the spatial resolution is higher than the "Abbe/Rayleigh" limit.

An advantage of the fluorescent microscope is that it is possible to switch the illumination from localization illumination to a structured illumination at any time. If for example, the switching mechanism comprises electro-optical light modulators the switching can be very fast (in a µs to ns range). A further advantage is that is possible to carry out individual structural illumination microscopy (SIM/SMI) and localization microscopy (LM) measurements as well as modified localization microscopy measurements which utilize structured illumination light with the same optical set-up. Accordingly, a fluorescence microscope with a less costly, less critical and more stable optical setup as compared to prior art solutions may be realized.

Further, the combination of the two different microscopic techniques, localization microscopy and structured illumination microscopy, in a single optical set-up allows to easily obtain images of the same region of interest in the object (sample) plane (x,y) in the same (coinciding) z-planes by both methods. This may be particularly advantageous for obtaining high resolution three-dimensional images of the sample and/or for obtaining images of the sample in which structural information obtained by structured illumination microscopy measurements is combined with localization information obtained by localization microscopy.

In an example, the fluorescent microscope may be configured to carry out a modified localization microscopy method using structured illumination during the process of acquiring localization image data. Surprisingly, it has been found out that the achievable localization precision when using structured activation light is higher than when using homogeneous, non-structured activation light as in conventional localization microscopy. In examples, the resolution may be improved by a factor of about 3 to 4 in comparison with conventional localization methods.

In an example, the structured illumination may be used to as a read-out (excitation) illumination during the process of obtaining localization microscopy images.

In particular, the localization illumination path may be configured and arranged such that the localization illumination light is capable of transferring at least a portion of the fluorescent molecules of the least one fluorescent label to an activatable ground state. The structured illumination path may be configured and arranged such that the structured illumination light is capable of transferring at least a portion of the fluorescent molecules of the least one fluorescent label from the ground state to an excited state, thereby emitting fluorescent light. The emitted fluorescent light may be detected by the image detector, thereby obtaining a localization microscopy image of the sample. The obtained image may be processed in the manner described in more detail below to obtain a super-resolution image/image data.

More specifically, the optical components forming the localization illumination path may be configured and arranged such that the localization illumination light has an intensity and/or wavelength suitable to activate at least a portion of the fluorescent molecules of the at least one fluorescent label, i.e. to transfer at least a portion of the fluorescent molecules into an activatable ground state. The optical components forming the structured illumination path may be configured and arranged such that the structured illumination light has an intensity and/or wavelength suitable to read-out at least a portion of the activated fluorescent molecules, i.e. to transfer at least a portion of the plurality of fluorescent molecules of the least one type fluorescent label from the ground state to an excited (activated) state, thereby emitting fluorescent light.

The intensity and/or the wavelength of the localization illumination light and the structured illumination light and/or the duration of illumination may be suitably selected depending on the characteristics of the at least one type fluorescent label. In particular, the illuminating the sample with localization illumination light and subsequently with structured illumination light may be such that in a given diffraction limited observation volume and at a given time, statistically only one fluorescing molecule of a given fluorescent label type is present. Thus for example, the intensity of the structured illumination light may be in the range of up to hundreds of Watts per square centimeter, while the localization light intensity may be in the range considerably over one Kilowatt per square centimeter.

This embodiment is particularly suitable when the sample is labelled with photo-switchable or photo-activatable fluorophores, such as for example PA-GFP, rsCherry, Dronpa, etc. These types of fluorescent labels are usually chemically modified (e.g. by adding appropriate side groups), in such a way that initially most of the fluorophores (i.e. the fluorescent molecules of the photo-switchable fluorophore label) are in an inactive state (not fluorescent dark state) for the fluorescence excitation at a given wavelength $\lambda_{exc}$. Upon illumination with activation light with a suitable wavelength $\lambda_{act}$ (for example in the near ultraviolet) and intensity, a portion of the fluorophores are "activated", i.e. are transferred to an activatable ground state. If the activation of the fluorophores is done stochastically by using low illumination intensity, only a few fluorophores within one acquisition time interval of the detector are activated. The activated fluorophores are subsequently excited to fluorescence (or read-out) with an excitation (read-out) light. The excitation light usually has a wavelength $\lambda_{exc}$ different from the wavelength of the activation light and a suitable, usually high, intensity. In other words, the activated fluorophores are transferred to a fluorescent state and from there to a dark state, thereby emitting fluorescent light, which is subsequently detected. Due to the low number of the active fluorophores, the detected signals from the individual fluorophores within a single image frame are spatially separated, so that super-resolution measurements may be carried out. Thus, optical isolation may be achieved. The final localization microscopy image may be obtained by registering a plurality of (e.g. about 10000 or more individual image frames with a high resolution enabling obtaining the positions of the individual molecules even if their mutual distances are far below the Abbe/Rayleigh limit.

Instead of (or in addition to) photo-switchable fluorophores "conventional" (generally non-switchable) fluorophores may be used. Examples of suitable "conventional" fluorophores also referred to as PHYMOD or SPDM/PHYMOD are disclosed in WO 2009/115244 A1 and include any of green fluorescent protein (GFP), yellow fluorescent protein (YFP), cyan fluorescent protein (CFP), orange fluorescent protein (OFP) and their derivates and/or modifications; monomeric red fluorescent protein (mRFP) and its derivatives and/or modifications derivatives (e.g. mCherry); rhodamin derivatives (e.g. Alexa- and/or attodyes); coumarin derivatives; xanthen derivatives, for example fluorescein; cyanin derivatives. Upon illumination with light having high intensity, for example in the range of 10 kW/cm$^2$ to 10 MW/cm$^2$, the fluorescent molecules are transferred in a metastable dark state. Upon continuing illumination with high intensity light (read-out light), the fluorescent molecules are stochastically transferred to a fluorescent state, from which they relax to a ground state, thereby emitting fluorescent light which is detected to form an image. Usually the wavelength of the activating light (the light used to transfer the fluorescent molecules to a metastable dark state) and the read-out light is the same.

In an example, the localization illumination path may be configured and arranged such that the localization illumination light is capable of transferring at least a portion of the fluorescent molecules of the at least one type fluorescent label into a dark state. The structured illumination path may be configured and arranged such that the structured illumination light is capable of stochastically transferring at least a portion of the fluorescent molecules of the at least one fluorescent label from the dark state to a fluorescent state, from which they relax to a ground state thereby emitting fluorescent light. The emitted fluorescent light may be detected by the image detector to form an image of the sample. The obtained image may be processed in the manner described in more detail below to obtain a super-resolution image/image data.

More specifically, the optical components forming the localization illumination path may be configured and arranged such that the localization illumination light has an intensity and/or wavelength suitable to transfer at least a portion (for example substantially all) of the fluorescent molecules of the at least one type fluorescent label into a non-fluorescent state, for example a reversibly bleached, dark state. In the following this state will be also referred to as temporary deactivated state, a metastable dark state or temporary dark state. The optical components forming the structured illumination path may be configured and arranged such that the structured illumination light has an intensity and/or wavelength suitable to stochastically transfer at least a portion of the fluorescent molecules from the metastable dark state to an excited (fluorescent) state, from which they relax to a ground state (for example a reversibly bleached state or irreversibly bleached state), thereby emitting fluorescent light. The intensity and/or the wavelength of the localization illumination light and the structured illumination light may be suitably selected depending on the characteristics of the at least one type fluorescent label. In particular, the intensity of the excitation light may be adjusted such that the bleaching rate of the fluorophores is approximately the same as the rate at which the fluorophores are returning from (i.e. a transferred from) the metastable dark state. Due to the low number of fluorophores transferred from the temporary (metastable) dark state, optical isolation may be achieved. The final localization microscopy image may be obtained by registering a plurality of (e.g. about 10000 or more individual image frames with a high resolution enabling discriminating the positions of the individual molecules even if their mutual distances are far below the Abbe/Rayleigh limit.

As described above, structured illumination light may be used during the process of acquiring localization images of a sample labelled for example with photo-switchable fluorophores or with "conventional" fluorophores exhibiting "blinking" behaviours, This is in contrast to conventional localization microscopy techniques which use homogenous, non-structured or pattern light has been used during the acquisition of the localisation image.

According to an example, suitably structured/patterned excitation (read-out) light may be utilized, for example illumination light which is spatially modulated in a transverse plane (i.e. in a plane perpendicular to the direction of propagation of the illumination light) and/or along the direction of propagation of the illumination light. In particular, the excitation light may be periodically modulated to form for example a sinusoidal grid or fringe pattern. Surprisingly, it has been found out that the achievable localization precision when using structured excitation light is higher than when using homogeneous, non-structured activation light.

The emitted fluorescent light and thus the detected intensity of the fluorescent light emitted from the individual fluorophores is modulated by the corresponding intensity of the excitation (read-out) light. The illumination of the sample with a plurality of illumination patterns, which are shifted with respect to each other results in a spatially dependent variation of the detected intensity of the fluorescent signal from each individual fluorophore. A comparison of the detected light intensities of the fluorescent light emitted from each individual fluorophore at the different positions of the excitation light pattern enables an improved localization of the individual fluorophores along the direction of variation or modulation of the excitation pattern. The intensity of the activation and/or excitation light and the integration time of the image detector (for example a CCD camera) may be selected and/or adjusted such that the total number of the possible fluorescent cycles (e.g. 10 000 cycles) of the fluorophores are run through within a limited number of image recordings.

The above procedure of obtaining a localization image using localization illumination with structured illumination excitation light may be repeated a plurality of times, thereby obtaining a plurality of localization microscopy images of the sample, wherein between each two localization image acquisitions the structured illumination pattern is phase-shifted and/or moved (for example translated and/or rotated).

In the following, a localization microscopy method using structured activation light as well as a corresponding reconstruction method will be de described in more detail.

For the sake of simplicity, it will be further assumed that the background signal and the detector noise are negligible. Further, a one-dimensional case will be considered. Of course, the method may be analogously extended to two or three dimensions.

It will be assumed that a fluorescent molecule (a fluorophore) is illuminated with a periodic sinusoidal intensity pattern Illu(x). It will be assumed that the sinusoidal illumination pattern Illu(x) having an amplitude between 0 and 2 and a period grid:

$$Illu(x) = \sin(x * k_{grid} - \varphi) + 1 \qquad (1)$$

$$k_{grid} = \frac{2\pi}{grid} \qquad (2)$$

The method is, however, equally applicable for other types of intensity patterns.

The image im of a localized fluorophore at the spatial position pos can be described by the following equation:

$$im = [A \cdot Illu(x) \cdot \delta(x-pos)] * h(x) \qquad (3)$$

In the above equation:
the symbol * denotes the convolution operation;
the filter h denotes Point Spread Function (PSF);
δ denotes the Dirac-Delta-Distribution (the spatial distribution of the point-like fluorophore);
A denotes the normalized intensity of an illuminated single fluorophore.
The full integral over the Point Spread Function h is normalized to be 1.

The detected signal is spatially integrated over a region which is significantly larger than the point spread function h (i.e. more than two times the FWHM of h) in order to acquire the total detected signal originating from a single fluorophore int. The total detected signal int is given by:

$$int = A\int[(\sin(x*k_{grid}-\varphi)+1 \cdot \delta(x-pos)]*h(x)dx. \qquad (4)$$

After integrating one obtains:

$$int = A[\sin(pos \cdot k_{grid}-\varphi)+1] \qquad (5)$$

In the above equation (5) A is the half of the maximum detectable intensity at a given positioning of the illumination pattern.

If equation (5) is solved with respect to the position of the fluorophore, one obtains:

$$pos = \frac{a\sin\left(\frac{int}{A} - 1\right) + \varphi}{k_{grid}} \qquad (6)$$

The precision of the position determination of the individual fluorophore depends number N of the detected photons. This number is subject to a poisson statistics. If N=int, one obtains:

$$\sigma(int) = \sqrt{int}. \qquad (7)$$

If the half of the maximum intensity A, the grid period $k_{grid}$ and the phase φ are known, the error in the determination of the position of the individual fluorophores depends only on the detected intensity:

$$\sigma(pos) = \frac{\partial pos}{\partial int}\sigma(int) \qquad (8)$$

$$\sigma(pos) = \frac{\partial pos}{\partial int}\sigma(int)$$

$$\sigma(pos) = \frac{\sqrt{int}}{k_{grid}A\sqrt{1 - \left(\frac{int}{A} - 1\right)^2}}$$

In case int=A (i.e. the fluorophore emits light with the half of the maximal intensity), one obtains:

$$\sigma(pos) = \frac{1}{k_{grid}\sqrt{int}} = \frac{grid}{2\pi\sqrt{int}} \qquad (9)$$

For conventional localization microscopy using uniform illumination light (for both activating and read-out), the precision of the localization is given by:

$$\sigma_{lok}(pos) = \frac{\sigma(h)}{\sqrt{int}}. \qquad (10)$$

Assuming that σ(h)=200 nm and grid=350 nm an improvement of the localization precision when structured illuminating light is used of factor 3.6 may be achieved.

Practically, A is unknown and has to be determined. One possible way to determine A is undertake a plurality of image recordings, wherein the illumination pattern is moved/shifted between each two subsequent image recordings. If for example, three individual recordings are undertaken and the illuminated pattern is shifted by $$\frac{2\pi}{3}$$

between two subsequent recordings, the sum of the signals from one fluorophore is given by:

$$int(\varphi) + int\left(\varphi + \frac{2\pi}{3}\right) + int\left(\varphi + \frac{4\pi}{3}\right) = 3A \qquad (11)$$

In order to determine the exact position of an individual fluorophore, a weighted average position may be determined from the individual positions pos obtained from the three individual images (image recordings) by applying equation (6) and the principle of the maximum-likelihood while taking into account the measured values of int and A and optionally taking further into account additional noise sources.

The position of the individual fluorophore may be initially fine determined on the basis of the periodic structure of the illumination within a single period of the illumination pattern. A coarse determination of the position of the individual fluorophore may be carried out by conventional localization of the fluorophore in the image data. This may be done by adding three subsequent images with the structured illumination pattern respectively phase-shifted by $$\frac{2\pi}{3}$$

and conducting a conventional localization algorithm (based for example on a center of gravity determination of the signal) on the sum image to coarsely determine the fluorophore position.

The coarse determination of the position of the individual fluorophores may for example be necessary to select the region/interval over which the signal integration is performed.

As noted above, the above method may be extended to the y- and/or z-dimension, in order to improve the localization precision in two and three dimensions. To achieve this, the illumination pattern has to be adjusted to have a modulation along the z-dimension.

Figure 1B:
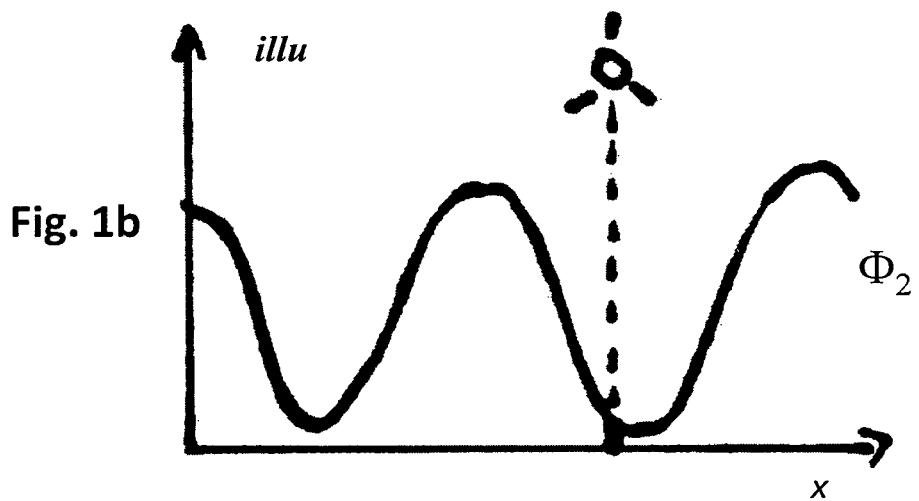
Figure 1C:
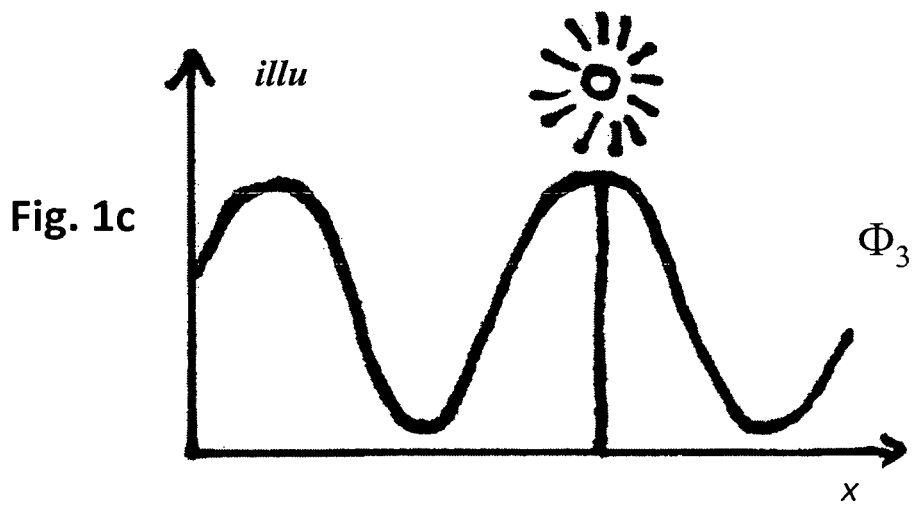

FIGS. 1a-1c show an example of using spatially modulated read-out light for excitation of the individual fluorescent molecules. The read-out illumination light has an intensity illu(x), which is sinusoidally modulated along x spatial direction and a phase $\Phi$. A localization image is recorded for three different phases, $\Phi_1$, $\Phi_2$ and $\Phi_3$ of the illumination pattern. As illustrated in FIGS. 1a-1c, the intensity of fluorescence of the individual fluorophore (fluorescent molecule) varies depending on the position/phase of the read-out illumination pattern. This allows a determination of the exact position of the individual fluorophore with improved precision, thus increasing the resolution in comparison to the conventional localization microscopy methods using substantially homogeneous (non-structured) illumination light.

Instead of using structured read-out (i.e. excitation) illumination light for the purposes of localization microscopy to selectively transfer a portion of the fluorescent molecules into a fluorescent state, it is possible to use the structured illumination path (and accordingly the structured illumination light) to selectively deactivate a portion of the activated fluorescent molecules, i.e. to selectively transfer a portion of the fluorescent molecules from a fluorescent state to a dark state.

In this case the localization illumination path may be configured and arranged such that the localization illumination light is capable of transferring at least a portion of the fluorescent molecules of the at least one type fluorescent label into a fluorescent active state. The structured illumination path may be configured and arranged such that the structured illumination light is capable of locally deactivating a portion of the activated fluorescent molecules that are in the fluorescent active state.

More specifically, the optical components forming the localization illumination path may be configured and arranged such that the localization illumination light has an intensity and/or wavelength suitable to transfer at least a portion (for example substantially all) of the fluorescent molecules of the at least one type fluorescent label into a fluorescent active state. The optical components forming the structured illumination path may be configured and arranged such that the structured illumination light has an intensity and/or wavelength suitable to deactivate the activated fluorescent molecules, i.e. to transfer at least a portion of the fluorescent molecules from an activated fluorescent state to an inactive (e.g. dark) state. The intensity of the structured illumination light may be selected such that only those fluorescent molecules that are located in areas of the sample in which the intensity of the structured illumination light is at or around its minimum remain in the fluorescent active state, whereas in all other areas the fluorescent molecules are deactivated.

In an example, the switching mechanism is switched to a first mode, in which the light emitted from the one or more light sources propagates through the localization illumination path, thereby illuminating the sample with (e.g. substantially homogeneous) localization illumination light. The wavelength, intensity and/or the duration of illumination may be suitably selected and/or adjusted, so that at least a portion of the fluorescent molecules (for example substantially all of the fluorescent molecules) is transferred into a fluorescent active state. Subsequently the switching mechanism is switched to a second mode, in which the light emitted from the one or more light sources propagates through the structured illumination path. A structured illumination pattern (for example a sinusoidal pattern) is projected onto the sample. The intensity, wavelength and/or the duration of structured illumination may be suitably selected, so that for example only few fluorescent molecules at or around the local minima of the projected structured illumination pattern remain in the fluorescent active state, whereas all other fluorescent molecules are deactivated. In other words, the wavelength, intensity and/or duration of illumination of the structured illumination light may be selected such that the probability that a given fluorophore/fluorescent molecule) will not be deactivated (and will therefore remain active) is high only in the area of a local minimum of the spatially modulated, structured illumination light. The limitation of the activated area results in an improvement of the achievable resolution as compared to conventional localization microscopy methods with homogeneous illumination.

FIG. 2a shows an example of structured illumination light with intensity $I_{off}$ which is sinusoidally modulated along the x spatial direction. FIG. 2b shows the probability $P_{on}$ that a given fluorescent molecule remains in an activated state (on-state) upon illumination with the structured illumination pattern shown in FIG. 2a. The fluorescent light emitted the remaining activated fluorescent molecules (i.e. of the non-deactivated fluorescent molecules) is detected by the image detector to form an image of the sample. As illustrated in FIG. 2b, the localization precision (i.e. the precision of spatial localization of the fluorescent bursts from the individual fluorescent molecules) depends on the size (for example width) of the active regions.

A plurality of localization images of the sample upon illuminating with structured deactivation illumination light may be detected by the image detector, wherein between each two image recordings the illumination pattern is phase-shifted and/or moved (for example shifted and/or rotated). At each phase-shift and/or position of the illumination pattern an image of the sample is acquired by detecting the fluorescent light from the individual non-deactivated fluorescent molecules. By illuminating the sample with phase-shifted and/or moved illumination pattern different fluorescent molecules are at or around the minimum of the illumination pattern and can be thus detected. In an example, at least three localization images are recorded, wherein between each two image recordings the phase of the $2\pi$ illumination pattern is shifted by $$\frac{2\pi}{3}.$$

Since the localization precision depends on the intensity of the structured, deactivating illumination light (deactivating pattern), theoretically it is possible to obtain unlimited resolution. In practice, the resolution may be improved by a factor of about 3 in comparison to conventional localization microscopy with homogeneous localization illumination light.

The above example of a localization microscopy using structured deactivating light is particularly suitable if the sample is labelled with photo-switchable fluorophores.

In yet another example, it is possible to serially carry out the image acquisition by means of structured illumination microscopy and by means of localization microscopy.

The localization illumination path (and more specifically the optical components forming the localization illumination path) may be configured and arranged such that the localization illumination light has an intensity and/or wavelength suitable to carry out measurements using the principles of (conventional) localization microscopy. The structured illumination path (and more specifically the optical components forming the structured illumination path) may be configured and arranged such that the structured illumination light has an intensity and/or wavelength suitable to carry out measurements using the principles of (conventional) structured illumination microscopy. The image detector may be configured to obtain at least one image of the sample illuminated with structured illumination light (structured illumination image) and at least one image of the sample illuminated with localization illumination light (localization illumination image).

The specific wavelength and/or intensity range may vary depending on the specific fluorescent label used, the sensitivity and/or acquisition time of the image detector, etc. and may be suitably selected by the skilled person. In particular, the intensity and/or the duration of illumination of the sample with localization illumination light may be such that in a given diffraction limited observation volume and at a given time, statistically only one fluorescing molecule of a given fluorescent label type is present.

The image detector may be configured to obtain a plurality of image frames of the sample illuminated with localization illumination light at different time steps, which are processed (e.g. merged) to obtain at least one super-resolution localization image. Each of the images acquired at each time step comprises a plurality of substantially spatially separated fluorescence signals from the single fluorescence molecules of the at least one type fluorescent label.

Further, the image detector may be configured to obtain a plurality of images of the fluorescently labelled sample, wherein each image is obtained at a different phase and/or position of the structured illumination pattern. The obtained images may be further processed by a data processing unit, to obtain a super-resolution structured illumination image of the sample.

Although conventional localization microscopy techniques allow obtaining positional information of individual (spatially separated) fluorophores/fluorescent molecules with very high precision and resolution, they only enable obtaining data regarding the positional information of individual fluorescent molecules/individual fluorophores. However, it is difficult to obtain data concerning continuous structures.

There exist various mathematical methods (for example Gauss blurring, triangulation, etc.) which enable the generation of such structures on the basis of the obtained localization microscopy data. However, these methods depend highly on the number of the detected individual signals. Accordingly, in many cases structural information is missing or is difficult to obtain.

In an example, a combined super-resolution image of the sample may be obtained by processing the obtained at least one (super-resolution) localization image and at least one (super-resolution) structured illumination microscopy image. The processing may for example comprise correlating the obtained super-resolution structured illumination image of the sample with the obtained at least one super-resolution localization image of the sample.

In order to allocate the localization data (i.e. the data obtained by means of localization microscopy) to the corresponding (continuous) structures obtained by structured illumination microscopy (which employs low intensity illumination and which is characterized by insignificant fluorophore bleaching), the image acquisition by means of structured illumination microscopy may be carried out before the actual measurement by localization microscopy (which employs high intensity illumination light and fluorophore bleaching).

The obtained (super-resolution) structured illumination microscopy image (or images) may serve as a high resolution overview image(s) of the observed sample. The structural information of the high resolution overview image(s) may be correlated with the information about the position of the individual fluorophores obtained by means of localization microscopy. The correlating may be performed by generating, based on the obtained structured illumination microscopy image, at least one mask, each mask defining a different region of interest within the sample. The mask may be obtained by applying a brightness threshold to the structured illumination microscopy image. The obtained at least one mask may be applied to the localization microscopy image, so that the localization microscopy image may be (separately) processed in each region of interest of the sample defined by the at least one mask to determine localization image data for each region of interest. The processing of the localization microscopy image in each region of interest may comprise a statistical analysis, for example to determine whether the obtained fluorescent signals from the individual fluorescent molecules are equally distributed, whether they are "clustered" in groups of different sizes, etc.).

FIGS. 3a-3c illustrate an example of obtaining a super-resolution microscopy image serially carrying out localization microscopy image acquisition and structured illumination microscopy image acquisition and by correlating the structured illumination microscopy and the localization microscopy image. FIG. 3a shows an exemplary localization microscopy image composed of the detected individual fluorescent signals. FIG. 3b shows an exemplary mask of one relevant region of interest obtained on the basis of the structured illumination microscopy image and FIG. 3c shows the localization microscopy image to which the mask shown in FIG. 3b is applied.

By applying the mask defining a region of interest within the sample, it is possible to for example to carry out a more exact statistical analysis of the positions of the individual fluorescent molecules within the sample. Since the analysis is carried out not on the whole localization microscopy image but separately for each region of interest, each region of interest being automatically determined based on the obtained high resolution overview structured illumination microscopy image, it is possible to improve the accuracy of the method and for example eliminate or reduce the errors due to variations in the image properties (such as brightness) caused for example by imperfect optics.

Localization microscopy (LM) usually delivers sparse datasets up to a point where the acquired localization microscopy image may consist of a set of single points showing no obvious connection. Structured illumination microscopy generating a high resolution image showing distinct continuous structures can be used to classify the single fluorophores detected with localization microscopy as belonging to a certain structure detected with structured illumination microscopy. By application of a classification method of this kind it becomes possible for example to statistically analyze the fluorophores belonging to certain structures which in the case of sparse fluorophore labelling might not be possible based on localization microscopy alone. Structured illumination microscopy delivers an orientation within a target as contextual information is provided, whereas localization microscopy is not always capable of this. In addition, in order to visualize localization microscopy data mathematical algorithm such as Gaussian blur or triangulation are of need in order to generate contextual information. However, this is highly dependent on the density of labelled targets and in some cases even impossible. Furthermore, the so obtained image is still not a "real" image.

The fluorescence microscope may further include a data processing unit configured to obtain super-resolution image of the sample or super-resolution image data based on the at least one image of the sample obtained by the image detector.

The data processing unit may be configured to carry out processing of the at least one image obtained by the image detector according to an aspect of the processing methods disclosed in the present application. The data processing unit may include an appropriately programmed general purpose processing chip, or a dedicated hardware. The processing unit may be connected to a data storage storing one or more of the images obtained by the image detector and may be configured to read data stored in the data storage.

According to another example, there is provided a method for obtaining super-resolution image data of a sample labeled with at least one type of fluorescent label, for example by using a fluorescent microscope as described above. The method includes illuminating the sample, thereby exciting at least a portion of the fluorescent molecules of the at least one fluorescent label to emit fluorescent light, the illuminating including illuminating the sample with localization illumination light (e.g. through the localization illumination path of the fluorescent microscope); and/or illuminating the sample with structured illumination light (e.g. through the structured illumination path of the fluorescent microscope). The method includes further detecting at least a portion of the fluorescent light emitted from the excited fluorescent molecules of the at least one fluorescent label, thereby obtaining at least one image of the illuminated sample and processing (for example by the data processing unit) the obtained at least one image of the sample to obtain super-resolution image data or a super-resolution image of the sample.

The sample may be serially illuminated with localization illumination light and structured illumination light (in any order) or may be simultaneously illuminated by both localization illumination light and structured illumination light at least during a part of the image acquisition process. The method may comprise switching between at least two of the different modes of illumination of the sample.

In an example, the illuminating the sample includes illuminating the sample with (e.g. substantially homogeneous) localization illumination light, thereby transferring at least a portion of the fluorescent molecules of the least one fluorescent label to an activatable ground state and subsequently illuminating the sample with structured illumination light, thereby transferring at least a portion of the fluorescent molecules of the least one fluorescent label from the ground state to an excited state, thereby emitting fluorescent light. The detecting includes detecting at least a portion of the fluorescent light emitted upon transfer of at least a portion of the fluorescent molecules of the least one fluorescent label from the ground state to an excited state.

The illuminating the sample with localization light and structured illumination light may be repeated for a plurality of phase-shifts and/or positions (e.g. translational shifts and/or rotations), thereby obtaining a plurality of images of the sample (each image corresponding to different phase shift and/or position of the structured illumination pattern). The obtained plurality of the images of the sample may be processed in the manner described above to obtain super-resolution image data or image(s) of the sample, for example two- or three dimensional image data or image(s).

In particular, as explained above, the processing of the obtained plurality of the images of the sample to obtain super-resolution image data or a super-resolution image of the sample may include:

processing each of the obtained plurality of images to determine a position ($pos_k$) of at least one individual fluorophore/fluorescent molecule, for example by applying the above equation (6); and determining a (weighted) average position pos from the determined positions ($pos_k$) of at least one individual fluorophore/fluorescent molecule, for example by applying the principle of the maximum-likelihood while taking into account the measured values of int und A und optionally taking further into account additional noise sources.

The above method is particularly suitable for obtaining super-resolution image data of samples labelled with photo-switchable fluorophores or a combination of photo-switchable fluorophores and naturally occurring autofluorescent substances in the sample. Accordingly, the method may further include the step of labelling the sample with at least type photo-switchable fluorophores.

In another example, the illuminating the sample includes Illuminating the sample with (e.g. substantially homogeneous) localization illumination light, thereby transferring at least a portion of the fluorescent molecules of the at least one type fluorescent label (for example substantially all fluorescent molecules) into a dark state; and subsequently illuminating the sample with the structured illumination light, thereby stochastically transferring at least a portion of the fluorescent molecules of the at least one fluorescent label from the dark state to a fluorescent state, from which they relax to a ground state, thereby emitting fluorescent light. The detecting may include detecting of the fluorescent light emitted upon said transfer of the at least a portion of the fluorescent molecules of the at least one fluorescent label from the dark state to the fluorescent state and from there to the ground state. The method may further include repeating the steps of illuminating the sample with localization light and structured illumination light and detecting the fluorescent light for a plurality of different phase shifts and/or positions of the structured illumination pattern, thereby obtaining a plurality of images of the sample; and processing the obtained plurality of the images of the sample to obtain super-resolution image data of the sample.

In particular, the processing of the obtained plurality of the images of the sample to obtain super-resolution image data or a super-resolution image of the sample may include:
  processing each of the obtained plurality of images to determine a position ($pos_k$) of at least one individual fluorophore/fluorescent molecule, for example by applying the above equation (6); and
  determining a (weighted) average position pos from the determined positions ($pos_k$) of at least one individual fluorophore/fluorescent molecule, for example by applying the principle of the maximum-likelihood while taking into account the measured values of int und A und optionally taking further into account additional noise sources.

The above method is particularly suitable for obtaining super-resolution image data of samples labelled with "conventional" fluorophores. Accordingly, the method may further include the step of labelling the sample with at least type of "conventional" fluorophores.

In an example the step of illuminating the sample may include Illuminating the sample with localization illumination light, thereby transferring at least a portion (for example substantially all) of the fluorescent molecules of the at least one type fluorescent label into a fluorescent active state, and subsequently illuminating the sample with structured illumination light, thereby locally deactivating a portion of the activated fluorescent molecules that are in the fluorescent active state. For example, the localization illumination light may be substantially homogeneous, i.e. non-patterned or structured.

The detecting may include detecting at least a portion of the fluorescent light emitted from the non-deactivated fluorescent molecules of the at least one fluorescent label, thereby forming an image of the sample.

The illuminating of the sample with localization light and structured illumination light may be repeated for a plurality of different phase shifts and/or positions of the structured illumination pattern, thereby obtaining a plurality of images of the sample. The obtained plurality of the images of the sample may be processed to obtain super-resolution image data of the sample, in the manner described in detail above.

This method is particularly suitable if the sample is labelled with photo-switchable fluorophores or a combination of photo-switchable fluorophores and naturally occurring autofluorescent substances. According the method may further include the step of labelling the sample with at least one type photo-switchable fluorophores.

In an example the illuminating the sample may include illuminating the sample with structured illumination light, thereby exciting at least a portion of the fluorescent molecules of the at least one fluorescent label to emit fluorescent light; and subsequently illuminating the sample with (e.g. substantially homogeneous, non-structured) localization illumination light, thereby exciting at least a portion of the fluorescent molecules of the at least one fluorescent label to emit fluorescent light. In other words, the illuminating the sample may include serially illuminating the sample with structured illumination light and with localization illumination light and obtaining corresponding images. The sample may be illuminated with structured illumination light and localization illumination light in any order.

For example, in the above example, since the intensity of the localization illumination light is usually higher than the average intensity of the structured illumination light, the sample is first illuminated with structured illumination light and then with localization illumination light. However, it is also possible (in particular with some fluorophores and/or embedding media) to first illuminate the sample with localization illumination light and then with structured illumination light. In this case, an appropriate time (for example from several minutes to up to 30 minutes) may be allowed to lapse between the illumination of the sample with localization illumination light and the illumination with structured illumination light. This time may be selected such as to allow for the fluorophores/fluorochromes to be analyzed to return to their state before the illumination with localization illumination light.

The detecting may include detecting at least a portion of the fluorescent light emitted by the fluorescent molecules of the at least one fluorescent label upon illumination of the sample with structured illumination light, therefore obtaining a structured illumination microscopy image of the sample, and detecting at least a portion of the fluorescent light emitted by the fluorescent molecules of the at least one fluorescent label upon illumination of the sample with the localization illumination light, therefore obtaining a localization microscopy image of the sample.

The processing step may include correlating the structured illumination microscopy image of the sample with the localization microscopy image of the sample to obtain super-resolution image data of at least one region of interest of the sample.

As explained above, generally localization microscopy technique only enables obtaining data regarding the positional information of individual fluorophores/fluorescent molecules. However, it is difficult to obtain data concerning continuous structures. There exist various mathematical methods, such as Gauss blurring, triangulation, etc., which enable the generation of such structures on the basis of the obtained localization microscopy data. However, these methods depend highly on the number of the detected individual signals. Accordingly, in many cases structural information is missing or is difficult to obtain.

In order to allocate the localization data (i.e. the data obtained by means of localization microscopy) to the corresponding (continuous) structures, according to an aspect it is proposed to carry out one or more measurements by means of structured illumination microscopy (which employs low intensity illumination and which is characterized by insignificant fluorophore bleaching) before the actual measurement by localization microscopy (which employs high intensity illumination light and fluorophore bleaching).

The obtained structured illumination microscopy image(s) may serve as a high resolution overview image(s) of the observed sample. The structural information of the high resolution overview image(s) may be correlated with the positional information of the individual fluorophores obtained by means of localization microscopy (i.e. on the basis of the localization microscopy image).

The correlation may include obtaining at least one mask defining a region of interest within the sample on the basis of the obtained structured illumination microscopy image, for example by applying a brightness threshold to the structured illumination image. The obtained mask(s) may be applied to the localization microscopy image. Thus, multiple relevant regions of interest within the sample may be analysed separately from each other in order to obtain localization image data, localization image data including data concerning the position of (at least a portion of) individual fluorescent molecules of the at least one fluorescent label.

The correlating step may include generating, based on the obtained structured illumination microscopy image, at least one mask, each mask defining a different region of interest within the sample, applying the at least one masks to the localization microscopy image and (separately) processing the localization microscopy image in each region of interest of the sample defined by the at least one mask to determine localization image data for each region of interest.

The processing of the localization microscopy image in each region of interest may include for example a statistical analysis to determine the distribution of the detected fluorescent signals of the individual fluorescent molecules in each of the region of interest, wherein the analysis may be carried out separately in each region of interest. Based on the statistical analysis various clustering algorithms may be applied in each region of interest defined by the masks. For example by means of statistical analysis it may be determined whether within each of the region of interest within the sample the detected fluorescent signals of the individual fluorescent molecules are equally distributed or whether they are divided in groups of a given size. Further, by applying the mask obtained on the basis of the structured illumination light microscopy image, it is possible to carry out a statistical analysis to obtain the exact position of the individual fluorescent molecules in the relevant region of interest defined by the mask.

Since the analysis is carried out not on the whole localization microscopy image but separately for each region of interest, each region of interest being automatically determined based on the obtained high resolution overview structured illumination microscopy image, it is possible to improve the accuracy of the method and for example eliminate or reduce the errors due to variations in the image properties (such as brightness) caused for example by imperfect optics.

Further, as described above Localization Microscopy (LM) usually delivers sparse datasets up to a point where the acquired localization microscopy image may consist of a set of single points showing no obvious connection. Structured illumination microscopy generating a high resolution image showing distinct continuous structures can be used to classify the single fluorophores detected with localization microscopy as belonging to a certain structure detected with structured illumination microscopy. By application of a classification method of this kind it becomes possible for example to statistically analyze the fluorophores belonging to certain structures which in the case of sparse fluorophore labelling might not be possible based on localization microscopy alone.

The sample may be labelled with "conventional" fluorophores and/or with photo-switchable and/or photo-activatable fluorophores as the at least one type fluorescent label. In addition or as alternative, autofluorescent properties of some naturally occurring substances in the sample may be advantageously used. The above method of serially carrying out structured illumination microscopy measurements and localization microscopy measurements is particularly suitable if "conventional" fluorophores are used for sample labelling.

Figure 4:
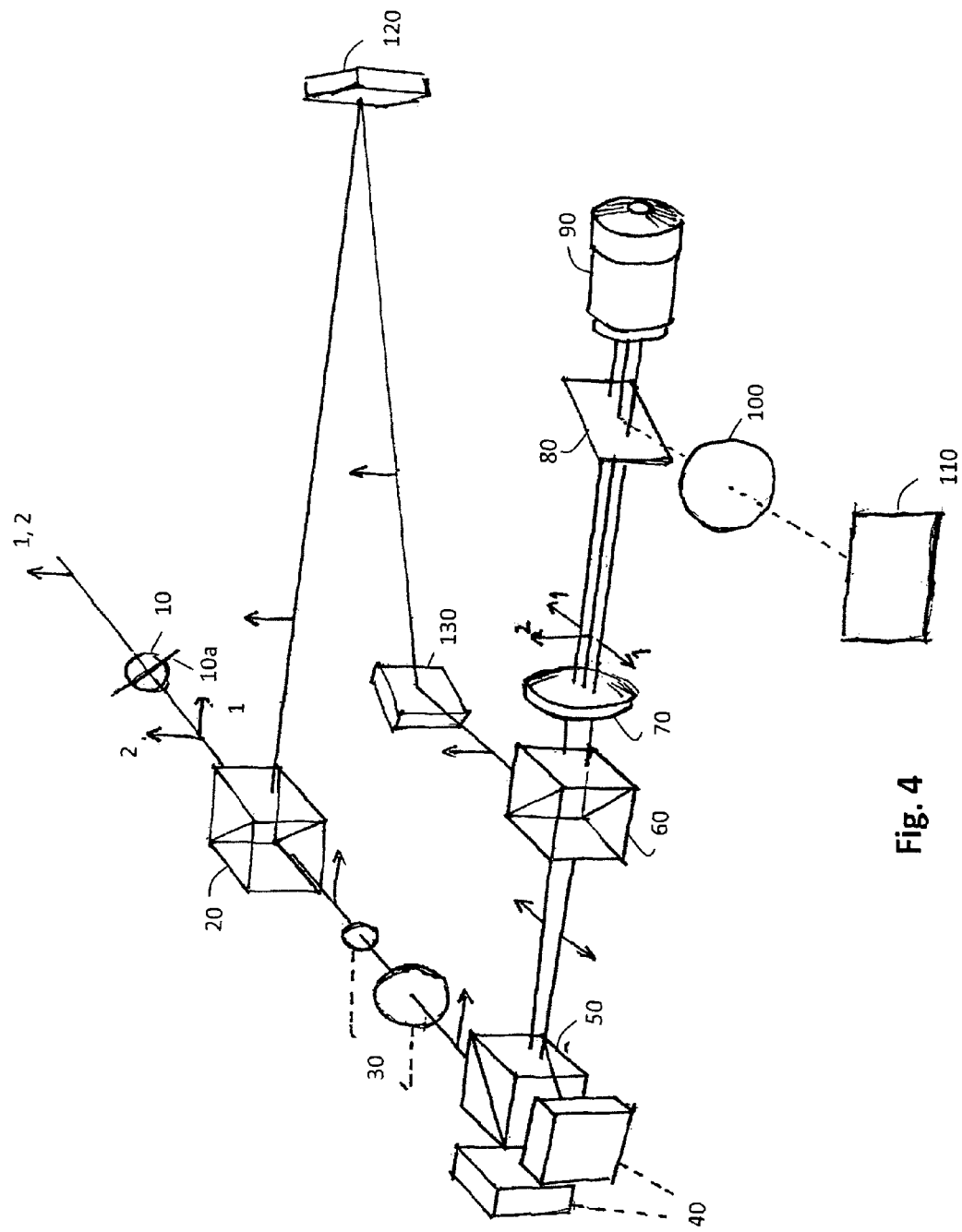
FIG. 4 shows a principle optical layout of a fluorescent microscope having structured illumination path and localization illumination path.

FIG. 4 shows an exemplary optical layout of a fluorescent microscope combining structured illumination microscope and localization illumination microscope in one optical set-up, wherein the switching of the different optical paths is based on polarization. In FIG. 4 the direction of polarization is indicated with an arrow pointing in the respective direction of polarization.

FIG. 4 shows only one possible optical layout, which can be modified by those skilled in the art in many other ways without departing from the scope of the disclosure.

The fluorescent microscope includes a light source (not shown) emitting light, for example circularly polarized light. In an example, the fluorescent microscope may include two light sources (not shown) emitting linearly polarized light with different polarization, for example a first light source emitting light with a first direction of polarization (in FIG. 4 indicated as polarisation "1") and a first wavelength and a second light source emitting light with a second direction of polarization (in FIG. 4 indicated as polarization "2") orthogonal to the first polarization and a second wavelength. The first and the second wavelengths may be equal or different. The at least one light source may be a laser, a LED, a gas discharge lamp or any other suitable light source.

The light emitted from the light source or light sources passes through an electro-optical modulator (EOM) 10. If the slow axis 10a of the EOM 10 is oriented at an angle of 45° with respect to the first polarization, the direction of the polarization of the light passing through the EOM may be rotated by applying a suitable electromagnetic field. Thus, the polarization of the light after the EOM 10 may be switched between the first polarization and the second polarization. The switching may be very fast, for example in the µs to ns range. Thus it is possible to switch over to the structured illumination during the process of stochastic blinking of the individual fluorophores, i.e. during the process of acquiring localization microscopic image.

After passing through the electro-optical modulator 10 the light is linearly polarized in one of the two orthogonal directions. By means of a polarizing beam splitter 20 (for example s-reflecting polarizing beam splitter) the linearly polarized light is directed either to the structured illumination path or to the localization illumination path. The electro-optical modulator to and the polarizing beam splitter 20 constitute the switching mechanism.

In an example, the polarizing beam splitter 20 transmits linearly polarized light with a first linear polarization. The transmitted light beam is expanded by a telescope system (beam expander) 30 and enters the pattern generation system, which in this specific example is constituted by a Michelson-Moore or a Twyman-Green interferometer. Other types of interferometers or pattern generation system may be used instead. The interferometer includes two mirrors 40 (which may be movable mirrors) and a non-polarizing beam splitter 50. The non-polarizing beam splitter 50 may be a rotatable beam splitter.

The interferometer produces an interference pattern (structured illumination light) in a lateral plane (i.e. in a plane which is substantially orthogonal to the direction of propagation of the structured illumination light beam. Advantageously at least one of the angular rotation, the fringe distance and the phase of the interference pattern may be adjusted/varied, for example by moving (translating, tilting and/or rotating) at least one of the mirrors 40 and/or by rotating the beam splitter 50.

It is also possible to configure the interferometer such that the structured illumination light is further spatially modulated in a third direction, for example in a direction of the propagation of the illumination light beam (z-direction). This may be achieved, for example, by inclining the interference plane with respect to the z-direction. Thus, for example, the interferometer may be configured and arranged such that the two interfering beams are not intersecting at equal opposite angles with respect to the z-direction, but at different angles, for example at angles of 60° and 0°, respectively. It is thus possible to achieve a precise localization of the fluorescent molecules also in a third dimension and to obtain three-dimensional high resolution images with improved accuracy. Other optical arrangements for obtaining three-dimensional high resolution images (or respectively three-dimensional high resolution structural data) are also possible.

The structured illumination light propagates through a polarizing beam splitter 60 (which may be a "s-reflecting" polarizing beam splitter), a focusing/converging lens 70, a dichroic beam splitter 80, capable of separating the illumination light and the fluorescent light emitted by the illuminated sample, and a microscope objective 90. The interference pattern is thus projected onto the sample to illuminate it with a laterally structured illumination light, i.e. with illumination light which is spatially modulated in a plane substantially orthogonal to the observation axis of the microscope and/or substantially parallel to the object plane (i.e. the plane in which the sample is arranged). Typically an area of about 3000 pm2 (~50 pm×50 pm) may be illuminated by the structured illumination light.

In an example the angle at which the sample is illuminated may be varied by rotating the beam splitter 50 and/or at least one of the mirrors 40. In particular, the angle at which the sample is illuminated may be adjusted to an angle suitable for total internal reflection illumination. In an example the focusing lens 70 and the objective 90 may be selected and arranged such as to form a collimator.

The fluorescence light emitted from the fluorescent molecules of the sample passes through the objective 90 and is reflected by the dichroic beam splitter 80 towards the tubular (imaging) lens 100. The fluorescent light passes through the tubular lens 100 and is detected by an image detector 110 (for example a CCD camera).

Linearly polarized light in a second direction, which is orthogonal to the first direction of polarization, it is reflected by the polarizing beam splitter 10 and enters the localization illumination path. The light reflected by the polarizing beam splitter 10 is reflected by mirrors 120 and 130 towards the polarizing beam splitter 60. After reflection at the polarizing beam splitter 60 the localization illumination light passes to through the focusing lens 70, the dichroic beam splitter 80 and the microscope objective 90 to illuminate the sample. Typically an area of about 100 pm2 to about 500 pm2 may be illuminated by the localization illumination light.

Figure 5A:
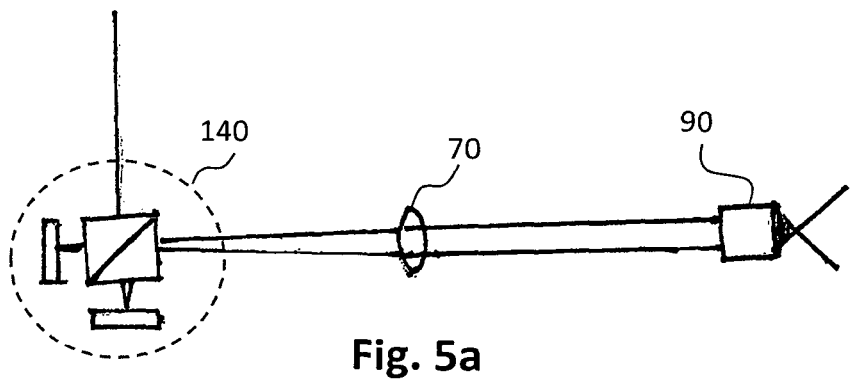
Figure 5B:
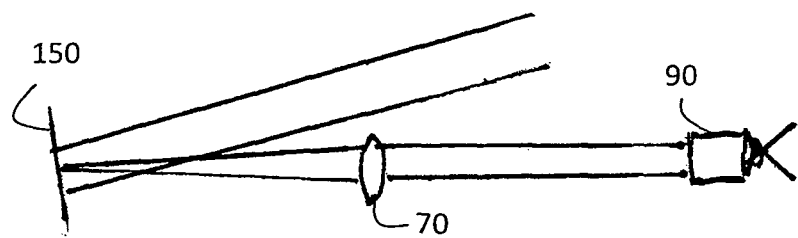
FIG. 5b shows a structured illumination path including a spatial light modulator.
Figure 5C:
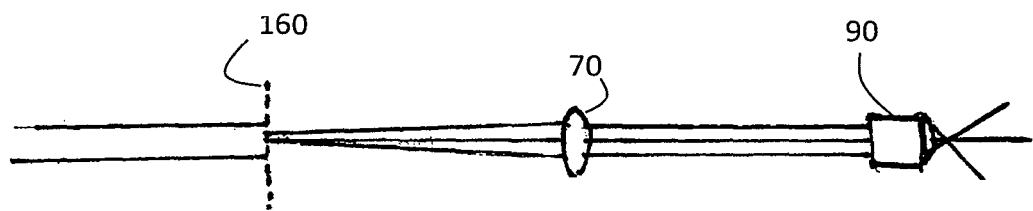
FIG. 5c shows a structured illumination path including a diffraction grating.

FIGS. 5a-5c show exemplary optical layouts of different structured illumination paths. In FIG. 5a structured illumination path includes a pattern generation system constituted by an interferometer 140; in FIG. 5b a pattern generation system constituted by a spatial light modulator (SLM) 150 and in FIG. 5c a pattern generation system constituted by a diffraction grating 160. The structured illumination light passes through a focusing/converging lens 70 and a microscope objective 90 to illuminate the sample.

In case a spatial light modulator 150 is used to structure (spatially modulate) the illumination light, it may be advantageous to arrange the spatial light modulator in a conjugated object plane. The use of spatial light modulator(s) to pattern the illumination light has the advantage that arbitrary patterns may be generated and projected onto the object plane. Further, fast change of the illumination patterns is possible.

In case a diffractive grating 160 is used to structure (spatially modulate) the illumination light, it may also be advantageous to arrange it a conjugated object plane. Advantageously, the diffractive grating is movable and may be rotated and/or translated. It is also possible to employ a pair of diffractive gratings rotating with respect to each other (e.g. in opposite directions) and to switch between the different diffractive gratings.

In further examples a similar optical set-up as shown in FIG. 4 may be used with the following modifications:

The light beam emitted from the at least one light source (e.g. a laser with suitably selected wavelength) may be expanded by a beam-expander, for example by means of a collimator, a telescope or the like arranged before or after the EOM 10. By means of the switching mechanism including for example a beam splitter 20 and EOM 10, the expanded light beam emitted from the at least one light sources may be redirected to either enter the structured illumination path or the localization microscopy illumination path.

Alternatively or in addition, in the localization illumination path there may be arranged a localization illumination adjustment unit configured to adjust the intensity of the light beam in the localization illumination path. In an example, the localization illumination adjustment unit may include or consist of at least one converging lens or a telescope configured to reduce or weakly increase (e.g. by a factor smaller as 10) the diameter of the light beam in the localization illumination path.

Further, the localization illumination path may be reflected at a mirror surface rotatable around at least one axis. The mirror surface may be arranged in a conjugated image plane. By varying the angle of rotation of the mirror surface, the angle at which the localization illumination light illuminates the sample (through the objective) may be varied. By suitably selecting the angle of rotation of the mirror surface, the sample may be illuminated with localization illumination light at an angle at which total internal reflection occurs at the interface of the coverslip holding the sample and the sample (or the medium embedding the sample). Thus, only the fluorophores in a thin layer at the interface with the coverslip may be excited to thereby form an image.

Figure 6:
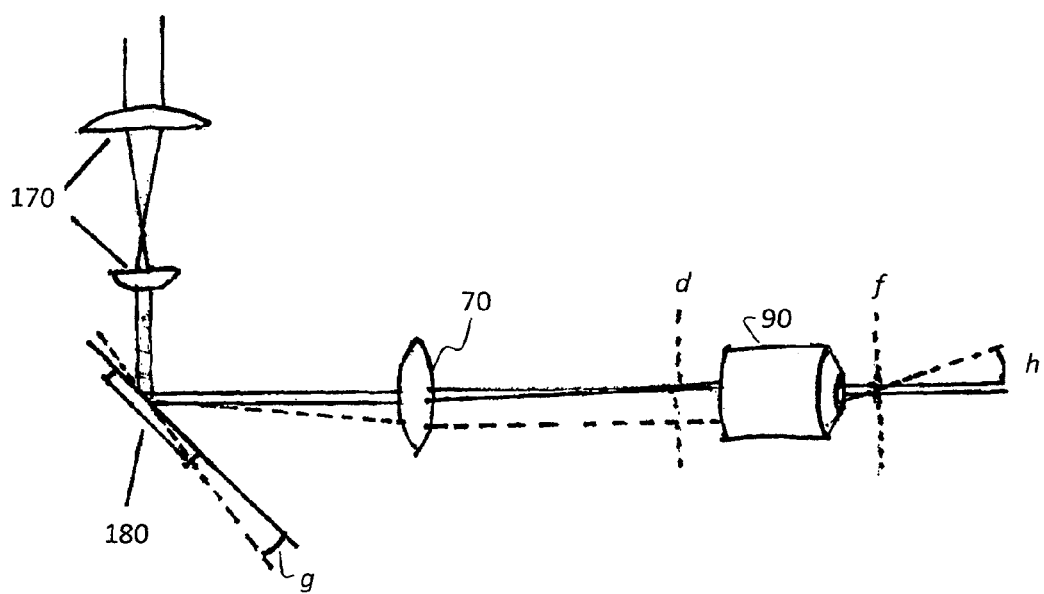

FIG. 6 shows an example of a localization illumination path (localization illumination light) being reflected at a mirror surface. The localization illumination path includes a telescope 170 (as a part of the localization illumination adjustment unit), which reduces the diameter of the localization light beam. The localization light beam is reflected at a rotatable mirror 180, arranged in a conjugated image plane. The localization light beam passes through a focusing/converging lens 70, which is arranged and configured to focus the light beam in the back focal plane "d" or in the front focal plane "f" of the objective 90. The mirror 180 may be a part of the localization illumination adjustment unit.

As shown in FIG. 6 by varying the angle of rotation, "g" of the mirror 180, the angle "h" of the localization illumination beam after the objective 90 (and accordingly the angle of illumination of the sample with localized illumination light) may be varied.

In the example shown in FIG. 4, the pattern generation system arranged in the structured illumination path is constituted by an interferometer. It is, however, possible to use other pattern generation systems, for example a pattern generation system including at least one spatial light modulator or a pattern generation system comprising at least one diffraction grating. The at least one SLM or diffraction grating may be configured to spatially modulate the intensity and optionally the phase of the expanded light beam which propagates through the structured illumination path to generate structured illumination light. In particular, the pattern generation system may be configured to spatially modulate the illumination light in a x-y plane (i.e. in a plane perpendicular to the axis of light beam propagation) and/or along the z-axis (i.e. along the axis of light beam propagation).

In the example shown in FIG. 4, the switching mechanism includes an electro-optical modulator 10 and a polarizing beam splitter 20. The switching between structured illumination path and the localization illumination path may be, however, realized in various other ways, for example by two movable and/or rotatable (dielectrical or metal) mirrors driven by stepper motors. In addition or as an alternative, it is possible to use other optical elements with polarization dependent transmission and/or reflection characteristics and to switch between the structured illumination path and localization illumination path by changing the polarization of the light beam emitted from the laser (immediately at the laser or elsewhere along the propagation path of the light beam). By using polarization dependent optical elements, it is possible to realize an optical set-up without mechanically movable optical elements. Thus, the stability of the optical set-up may be improved and the errors due to mechanically movable parts reduced.

Further, in FIG. 4 the electro-optical modulator 10 (or other switching element) is arranged before the illumination light is diverted towards the structured illumination path and/or the localization illumination path. However, it is possible to realize an optical set-up in which the EOM (or other switching element) is arranged at the end (i.e. after) the structured illumination path and the localization illumination path.

In addition, in the example shown in FIG. 4 the objective is shared by both the illumination system and the detection system (comprising the image detector and optionally the tubular lens 100). The detection system may, however, include a second objective, for example a second opposing objective arranged and configured to produce an image of sample formed by the fluorescent light emitted from the fluorescently labeled sample. The second objective may be arranged such as to be opposite to the objective through which the sample is illuminated.

Other modifications of the optical set-up shown in FIG. 4 are possible without departing from the scope of the disclosure.

In operation of the fluorescent microscope the switching mechanism may be initially switched to a first mode, in which illumination light linearly polarized in the second direction propagates through the localization illumination path to illuminate the sample with (e.g. substantially homogeneous) localization illumination light. The wavelength, intensity and/or the duration of illumination may be suitably selected and/or adjusted, so that an image of the sample is acquired by the image detector 100 by means of localization microscopy as explained above. Thereafter, the switching mechanism may be switched to a second mode, in which illumination light linearly polarized in the first direction propagates through the structured illumination path to illuminate the sample with structured localization illumination light. The wavelength, intensity and/or the duration of illumination may be suitably selected and/or adjusted, so that at least one image of the sample (structured illumination image) is acquired by means of structured illumination microscopy. The order in which the localization illumination image and the structured illumination image are obtained may of course be reversed.

The two images may be subjected to processing to obtain a combined super-resolution image of the sample as explained above in connection with FIGS. 3a-3c. In particular, based on the obtained structured illumination microscopy image, at least one mask defining a region of interest within the sample may be generated (for example by performing a brightness threshold operation). The mask may be applied to the localization microscopy image. The localization image within the region of interest defined by the mask may be processed (for example by performing statistical analysis of the distribution of the individual localized fluorophores) to determine localization image data for the specific region of interest. Multiple masks may be generated based on the structured illumination image, each mask defining a different region of interest.

Alternatively a super-resolution image of the sample may be acquired by the image detector 100 by employing modified localization microscopy method using structured illumination light to excite or to deactivate fluorescent molecules during the process of localization microscopy, as described above.

In an example the switching mechanism may be initially switched to a first mode, in which illumination light being linearly polarized in a second direction propagates through the localization illumination path to illuminate the sample with (substantially homogeneous) localization illumination light. Depending on the type of labelling of the sample, the wavelength, intensity and/or the duration of illumination may be suitably selected and/or adjusted, so that a portion of the fluorescent molecules is transferred into an activatable ground state (if for example photo-switchable fluorophores are used) or so that at least a portion (for example all) of the fluorescent molecules is transferred into a temporary dark state (if for example "conventional" fluorophores are used).

Subsequently, the switching mechanism may be switched to a second mode, in which illumination light linearly polarized in the first direction propagates through the structured illumination path to illuminate the sample with structured localization illumination light (for example a sinusoidal pattern such as shown in FIG. 1a-1c). The intensity, wavelength and/or the duration of structured illumination may be suitably selected, so that the activated fluorophores are excited to a fluorescent state (if for example photo-switchable fluorophores are used) or so that the fluorescent molecules are stochastically transferred from the temporary dark state to a fluorescent state (of for example "conventional" fluorophores are used). The fluorescent light emitted thereby is detected by the image detector 100 to form a localization microscopy image of the sample.

The above procedure may be repeated multiple times for a plurality of different phases of the structured illumination pattern, thereby obtaining a plurality of localization microscopy images of the sample. In an example, three localization microscopy images of the sample may be obtained, wherein between two images the phase of the illumination pattern is shifted by $$\frac{2\pi}{3},$$

as described above in connection with FIGS. 1a-1c. The acquired plurality of localization microscopy images may be subjected to a processing in the manner describe above in connection with FIGS. 1a-1c and equations (1) to (11).

In particular, the positions of the individual fluorophores may be determined in each of the obtained localization microscopy images (see equation (6)). The exact positions of the individual fluorophores may be determined by determining respective weighted average positions from the determined individual positions pos in each of the localization microscopy images by applying the principle of the maximum-likelihood while taking into account the measured values of int und A und optionally taking further into account additional noise sources.

In still another example, the structured illumination light may be used to selectively deactivate activated fluorescent molecules in the manner described above in connection with FIGS. 2a-2b.

For example the switching mechanism may be initially switched to a first mode, in which illumination light linearly polarized in a second direction propagates through the localization illumination path to illuminate the sample with (e.g. substantially homogeneous) localization illumination light. The wavelength, intensity and/or the duration of illumination may be suitably selected and/or adjusted, so that at least a portion of the fluorescent molecules is transferred into a fluorescent active state. In an example a major portion or substantially all of the fluorescent molecules are transferred into a fluorescent active state, as shown in FIG. 2a.

Subsequently, the switching mechanism is switched to a second mode, in which a structured illumination pattern (for example a sinusoidal pattern) is projected onto the sample. The intensity, wavelength and/or the duration of structured illumination may be suitably selected, so that for example only few fluorescent molecules at or around the local minima of the projected structured illumination pattern remain in the fluorescent active state, whereas all other fluorescent molecules are deactivated, as shown in FIG. 2b.

The fluorescent light of the remaining activated fluorescent molecules (i.e. of the non-deactivated fluorescent molecules) is detected by the image detector to form a localization microscopy image of the sample.

The above procedure may be repeated a plurality of times, wherein between each two image acquisitions the illumination pattern is phase-shifted and/or moved (for example shifted and/or rotated). At each phase-shift and/or position of the illumination pattern a localization microscopy image of the sample is acquired by detecting the fluorescent light from the individual non-deactivated fluorescent molecules. By illuminating the sample with phase-shifted and/or moved illumination pattern different fluorescent molecules are at or around the minimum of the illumination pattern and can be thus detected. In an example, at least three localization images are recorded, wherein between each two image recordings the $2\pi$ phase of the illumination pattern is shifted by $$\frac{2\pi}{3}.$$

Since the localization precision depends on the intensity of the structured, deactivating illumination light (deactivating pattern), theoretically it is possible to obtain unlimited resolution. In practice, the resolution may be improved by a factor of about 2 to 4 in comparison to conventional localization microscopy with homogeneous localization illumination light.

The above example using structured deactivating light is particularly suitable if the sample is labelled with photoswitchable fluorophores.

In the above examples employing a modified localization microscopy method using structured illumination light to excite or deactivate fluorescent molecules during the process of localization microscopy the switching mechanism is configured to switch between either localization illumination (first mode) or the structured illumination (second mode). The switching mechanism may, however, be configured to switch between a first mode, wherein the light from the at least one light source propagates through the localization illumination path and a third mode, wherein a portion of the light from the at least one light source propagates through the localization illumination path and another portion through the structured illumination path. For example, the microscope may include a plurality of light sources and in the third mode, the light from one light source may travel through the localization illumination path and the light from another light source may travel through the structured illumination path. Thus, the sample may be initially illuminated by a localization illumination light, to for example activate at least a portion of the fluorescent molecules as described above. Subsequently, the switching mechanism may switch to the third mode, so that the sample is illuminated with structured illumination light, while continuing to illuminate it with localization illumination light. The structured illumination light may selectively excite or deactivate the activated molecules and an image of the sample may be formed by the image detector by detecting fluorescent light emitted from the excited/activated fluorescent molecules.

The invention claimed is:

1. A fluorescence microscope for obtaining super-resolution images of a sample labeled with at least one fluorescent label by combining localization microscopy and structured illumination microscopy, the microscope comprising:
   one or more light sources;
   an illumination system having a structured illumination path for illuminating the sample with structured illumination light and a localization illumination path for illuminating the sample with localization illumination light, wherein the illumination system comprises:
   a switching mechanism (10, 20) configured to switch between at least two of a first mode, a second mode, and a third mode, wherein
      in the first mode at least a portion of the light emitted from the one or more light sources propagates through one of the illumination paths;
      in the second mode at least a portion of the light emitted from the one or more light sources propagates through the other one of the illumination paths; and
      in the third mode at least a portion of the light emitted from one or more of the light sources propagates through one illumination path while simultaneously at least another portion of the light emitted from one or more of the light sources propagates through the other illumination path;
   a pattern generation system (140; 150; 160) positioned in the structured illumination path, said pattern generation system (140; 150; 160) configured to spatially modulate the intensity of the light which entered the structured illumination path in at least one spatial direction, thereby generating the structured illumination light; and at least one image detector (110) positioned in an optical detection path, the at least one image detector configured to detect at least a portion of fluorescent light emitted from fluorescent molecules of the illuminated sample, thereby obtaining an image of the sample;

wherein:
i) the localization illumination path is configured and arranged such that the localization illumination light is capable of transferring at least a portion of the fluorescent molecules of the at least one fluorescent label to an activatable ground state, and the structured illumination path is configured and arranged such that the structured illumination light is capable of transferring at least a portion of the fluorescent molecules of the at least one fluorescent label from the ground state to an excited state, thereby emitting fluorescent light;

ii) the localization illumination path is configured and arranged such that the localization illumination light is capable of transferring at least a portion of the fluorescent molecules of the at least one fluorescent label into a dark state, and the structured illumination path is configured and arranged such that the structured illumination light is capable of stochastically transferring at least a portion of the fluorescent molecules of the at least one fluorescent label from the dark state to a fluorescent state, from which they relax to a ground state thereby emitting fluorescent light; or iii) the localization illumination path is configured and arranged such that the localization illumination light is capable of transferring at least a portion of the fluorescent molecules of the at least one fluorescent label into a fluorescent active state, and the structured illumination path is configured and arranged such that the structured illumination light is capable of locally deactivating a portion of the activated fluorescent molecules that are in the fluorescent active state.

2. The fluorescence microscope according to claim 1, wherein the switching mechanism (10, 20) is configured to successively switch between the first mode and the second mode.

3. The fluorescence microscope according to claim 1, wherein the switching mechanism (10, 20) is configured to switch between the first mode and the third mode.

4. The fluorescence microscope according to claim 1, wherein the illumination system further comprises an illumination adjustment unit (170, 180) configured to adjust at least one of:
the intensity of at least one of the localization illumination light and the structured illumination light;
the angle of illumination of the sample with at least one of the localization illumination light and the structured illumination light; and
the duration of illumination of the sample with at least one of the localization illumination light and the structured illumination light.

5. The fluorescence microscope according to claim 1, wherein
the fluorescence microscope further comprises a data processing unit configured to obtain super-resolution image of the sample based on the at least one image of the sample obtained by the image detector (100).

6. A method for obtaining super-resolution image data of a sample labeled with at least one type of fluorescent label by using a fluorescent microscope in accordance with claim 1, the method comprising:
illuminating the sample, thereby exciting at least a portion of the fluorescent molecules of the at least one fluorescent label to emit fluorescent light, said illuminating the sample comprising illuminating the sample with localization illumination light and illuminating the sample with structured illumination light, the structured illumination light having intensity which is spatially modulated in at least one spatial direction;
detecting at least a portion of the fluorescent light emitted from the excited fluorescent molecules of the at least one fluorescent label, thereby obtaining at least one image of the illuminated sample; and
processing the obtained at least one image of the sample image to obtain super-resolution image data.

7. A method for obtaining super-resolution image data of a sample labeled with at least one type of fluorescent label by using a fluorescent microscope, the method comprising:
illuminating the sample, thereby exciting at least a portion of the fluorescent molecules of the at least one fluorescent label to emit fluorescent light, said illuminating the sample comprising illuminating the sample with localization illumination light and subsequently illuminating the sample with structured illumination light, the structured illumination light having intensity which is spatially modulated in at least one spatial direction, wherein illuminating the sample with localization illumination light and subsequently illuminating the sample with structured illumination light comprises:
i) transferring at least a portion of the fluorescent molecules of the at least one fluorescent label to an activatable ground state and subsequently transferring at least a portion of the fluorescent molecules of the at least one fluorescent label from the ground state to an excited state;
ii) transferring at least a portion of the fluorescent molecules of the at least one type fluorescent label into a dark state and subsequently stochastically transferring at least a portion of the fluorescent molecules of the at least one fluorescent label from the dark state to a fluorescent state, from which they relax to a ground state; or
iii) transferring at least a portion of the fluorescent molecules of the at least one type fluorescent label into a fluorescent active state and subsequently locally deactivating a portion of the activated fluorescent molecules that are in the fluorescent active state;
detecting at least a portion of the fluorescent light emitted from the excited fluorescent molecules of the at least one fluorescent label, thereby obtaining at least one image of the illuminated sample, wherein detecting at least a portion of the fluorescent light comprises:
i) detecting at least a portion of the fluorescent light upon transfer of at least a portion of the fluorescent molecules of the at least one fluorescent label from the ground state to an excited state;
ii) detecting at least a portion of the fluorescent light upon said transfer of the at least a portion of the fluorescent molecules of the at least one fluorescent label from the dark state to the fluorescent state and from there to the ground state; or iii) detecting at least a portion of the fluorescent light emitted from the non-deactivated fluorescent molecules of the at least one fluorescent label;

repeating the steps of illuminating the sample with localization light and structured illumination light and detecting at least a portion of the emitted fluorescent light for a plurality of different phase shifts and/or positions of the structured illumination light pattern, thereby obtaining a plurality of images of the sample; and processing the obtained plurality of images of the sample to obtain super-resolution image data.

* * * * *